US010058244B2

(12) United States Patent
Raymond et al.

(10) Patent No.: US 10,058,244 B2
(45) Date of Patent: *Aug. 28, 2018

(54) ANGULAR MULTIPLEXED OPTICAL COHERENCE TOMOGRAPHY SYSTEMS AND METHODS

(71) Applicant: AMO WaveFront Sciences, LLC, Santa Ana, CA (US)

(72) Inventors: Thomas D. Raymond, Edgewood, NM (US); Devon E. Reid, Thorton, CO (US)

(73) Assignee: AMO Wavefront Sciences, LLC, Santa Ana, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/343,750

(22) Filed: Nov. 4, 2016

(65) Prior Publication Data

US 2017/0071467 A1    Mar. 16, 2017

Related U.S. Application Data

(63) Continuation of application No. 14/864,730, filed on Sep. 24, 2015, now Pat. No. 9,486,137, which is a
(Continued)

(51) Int. Cl.
*A61B 3/14* (2006.01)
*A61B 3/00* (2006.01)
(Continued)

(52) U.S. Cl.
CPC ............ *A61B 3/102* (2013.01); *A61B 3/1005* (2013.01); *A61B 3/107* (2013.01); *A61B 5/0066* (2013.01);
(Continued)

(58) Field of Classification Search
CPC ......... A61B 3/102; A61B 3/14; A61B 3/0025; G01B 9/02091; G01B 9/02044
(Continued)

(56) References Cited

U.S. PATENT DOCUMENTS

| 4,665,913 A | 5/1987 | L'Esperance, Jr. |
| 4,669,466 A | 6/1987 | L'Esperance |

(Continued)

FOREIGN PATENT DOCUMENTS

| EP | 2565625 A1 | 3/2013 |
| WO | 03012405 A2 | 2/2003 |

OTHER PUBLICATIONS

Grulkowski I., et al., "Retinal, Anterior Segment and Full Eye Imaging Using Ultrahigh Speed Swept Source OCT with Vertical-Cavity Surface Emitting Lasers," Biomedical Optics Express, 2012, vol. 3 (11), pp. 2733-2751.
(Continued)

*Primary Examiner* — Mohammed Hasan
(74) *Attorney, Agent, or Firm* — Johnson & Johnson Surgical Vision, Inc.

(57) ABSTRACT

Angle multiplexed optical coherence tomography systems and methods can be used to evaluate ocular tissue and other anatomical structures or features of a patient. The angle multiplexed optical coherence tomography system includes a light source, an optical assembly for obtaining a plurality of sample beams corresponding to respective anatomical locations of the eye of the patient, where individual sample beams are associated with a respective non-zero angle relative to a reference beam, and a detection mechanism that detects individual unique interference patterns respectively provided by the plurality of sample beams, for simultaneous evaluation of the anatomical locations.

10 Claims, 16 Drawing Sheets

Related U.S. Application Data continuation of application No. 14/199,161, filed on Mar. 6, 2014, now Pat. No. 9,198,573.

(60) Provisional application No. 61/794,276, filed on Mar. 15, 2013.

(51) Int. Cl.
    *A61B 3/10* (2006.01)
    *A61B 3/107* (2006.01)
    *A61B 5/00* (2006.01)
    *G01N 21/47* (2006.01)
    *G01B 9/02* (2006.01)

(52) U.S. Cl.
    CPC ....... *G01B 9/0205* (2013.01); *G01B 9/02087* (2013.01); *G01B 9/02091* (2013.01); *G01N 21/4795* (2013.01)

(58) Field of Classification Search
    USPC .................................................. 351/200–246
    See application file for complete search history.

(56) References Cited

U.S. PATENT DOCUMENTS

| | | | |
|---|---|---|---|
| 4,732,148 A | 3/1988 | L'Esperance, Jr. | |
| 4,770,172 A | 9/1988 | L'Esperance, Jr. | |
| 4,773,414 A | 9/1988 | L'Esperance, Jr. | |
| 5,108,388 A | 4/1992 | Trokel et al. | |
| 5,163,934 A | 11/1992 | Munnerlyn | |
| 5,207,668 A | 5/1993 | L'Esperance, Jr. | |
| 5,219,343 A | 6/1993 | L'Esperance, Jr. | |
| 5,459,570 A | 10/1995 | Swanson et al. | |
| 5,491,524 A * | 2/1996 | Hellmuth ............... | A61B 3/102 351/205 |
| 5,537,162 A * | 7/1996 | Hellmuth ............... | A61B 3/102 351/206 |
| 5,646,791 A | 7/1997 | Glockler | |
| 5,683,379 A | 11/1997 | Hohla | |
| 5,713,892 A | 2/1998 | Shimmick | |
| 5,807,379 A | 9/1998 | L'Esperance, Jr. | |
| 6,004,313 A | 12/1999 | Shimmick et al. | |
| 6,095,651 A | 8/2000 | Williams et al. | |
| 6,203,539 B1 | 3/2001 | Shimmick et al. | |
| 6,271,915 B1 | 8/2001 | Frey et al. | |
| 6,315,413 B1 | 11/2001 | Shimmick et al. | |
| 6,331,177 B1 | 12/2001 | Munnerlyn et al. | |
| 6,396,587 B1 | 5/2002 | Knupfer et al. | |
| 6,775,007 B2 | 8/2004 | Izatt et al. | |
| 7,061,662 B2 | 6/2006 | Chung et al. | |
| 7,072,047 B2 | 7/2006 | Westphal et al. | |
| 7,733,497 B2 | 6/2010 | Yun et al. | |
| 8,348,429 B2 | 1/2013 | Walsh et al. | |
| 9,198,573 B2 | 12/2015 | Raymond et al. | |
| 9,486,137 B2 * | 11/2016 | Raymond ............... | A61B 3/102 |
| 2010/0157309 A1 | 6/2010 | Tearney et al. | |
| 2010/0181462 A1 | 7/2010 | Sugita | |
| 2011/0009701 A1 | 1/2011 | Feldman et al. | |
| 2011/0306875 A1 | 12/2011 | Fischer et al. | |

OTHER PUBLICATIONS

Hauger C., et al., "Interferometer for Optical Coherence Tomography," Applied Optics, 2003, vol. 42 (19), pp. 3896-3902.

International Search Report and Written Opinion for Application No. PCT/US2014/021147, dated Jul. 1, 2014, 13 pages.

Koch P., et al., "Linear Optical Coherence Tomography System with a Downconverted Fringe Pattern," Optics Letters, 2004, vol. 29 (14), pp. 1644-1646.

Mrochen M., et al., "Optical Ray Tracing for the Calculation of Optimized Corneal Ablation Profiles in Refractive Treatment Planning," Journal of Refractive Surgery, 2008, vol. 24 (4), pp. S446-S451.

Podoleanu A.G., et al., "Simultaneous Low Coherence Interferometry Imaging at Two Depths Using an Integrated Optic Modulator," Optics Communications, 2001, vol. 191 (1-2), pp. 21-30.

Wojtkowski M., et al., "Full Range Complex Spectral Optical Coherence Tomography Technique in Eye Imaging," Optics Letters, 2002, vol. 27 (16), pp. 1415-1417.

Wojtkowski M., "High-Speed Optical Coherence Tomography: Basics and Applications," Applied Optics, 2010, vol. 49 (16), pp. D30-D61.

Zysk A.M., et al., "Projected Index Computed Tomography," Optics Letters, 2003, vol. 28 (9), pp. 701-703.

\* cited by examiner

ANGULAR MULTIPLEXED OPTICAL COHERENCE TOMOGRAPHY SYSTEMS AND METHODS

CROSS-REFERENCES TO RELATED APPLICATIONS

This application is a continuation application under 35 USC § 120 of U.S. patent application Ser. No. 14/864,730, filed Sep. 24, 2015, Now U.S. Pat. No. 9,486,137 B2, which is a continuation application under 35 USC § 120 of U.S. patent application Ser. No. 14/199,161, filed Mar. 6, 2014 and issued on Dec. 1, 2015 as U.S. Pat. No. 9,198,573, which claims priority to U.S. Provisional application No. 61/794,276, filed on Mar. 15, 2013. The entire contents of the above three applications are incorporated herein by reference.

BACKGROUND OF THE INVENTION

Optical Coherence Tomography (OCT) is used in the ophthalmic industry in pachymetry, anterior chamber depth, axial length, and retinal imaging applications. Known OCT systems typically use either a time domain or a spectral domain technology to provide line of sight length optical analogs of the echoes in ultrasonic imaging via homodyne detection. With the use of broadband sources, there is homodyne signal amplitude when the reference and signal beams are sufficiently close in optical delay. Time domain and spectral domain OCT use collinear reference and signal beams to achieve a detectable interference that includes the depth information.

Currently known OCT systems involving axial measurements may be negatively impacted by axial or transverse eye movement during the measurement. For example, existing time domain measurements techniques used to measure axial length may be prone to such errors where a mirror must be physically scanned to scan the depth range. Relatedly, many currently known spectral domain methods typically do not afford the depth of range desirable for axial length measurements because the depth range is determined by the spectral resolution of the spectrometer/detector combination. In many instances, the range which may be obtained from such instruments is effectively limited to a maximum of about 5 mm. In addition, existing spectral domain OCT techniques may be prone to ghost images.

Some have proposed multiple spectral domain OCT systems with offset axial depth locations, single or multiple SLD sources for use with separate spectrometers for each depth, and the implementation of switchable time delay references (e.g., using fiber switches with different length fibers) for spectral domain OCT to address these limitations. However, many time such proposals suffer from high costs.

Hence, although current techniques may provide real benefits to those in need, still further improvements may be desirable. Embodiments of the present invention provide solutions to at least some of these outstanding needs.

BRIEF SUMMARY OF THE INVENTION

Embodiments of the present invention encompass the use of highly precise OCT techniques, which are particularly useful for noninvasive evaluation of the optical characteristics of the human eye or other tissues, and can be used to enhance or supplement other optical evaluation modalities such as topography and/or wavefront sensing. For example certain OCT approaches can be used to asertain a range distance for use with topography procedures, and/or to measure internal distance features present within the eye. In some cases, OCT techniques as discussed herein can be used to precisely evaluate the distance between an optical element (e.g. final lens) of a optical system device and an optical feature (e.g. corneal apex) of the eye. Accordingly, embodiments of the present invention encompass systems and methods for obtaining extremely low surface uncertainties, for example on the order of a fraction of a micron. Topography measurements obtained in conjuction with such techniques can provide a highly accurate diagnostic evaluation for a patient eye, and such approaches are well suited for use in evaluating corneal morphology and/or pathology, at times before, during, or after surgery.

Embodiments of the present invention encompass systems and methods for evaluating optical tissue in an eye of a patient and for other medical imaging purposes. Exemplary techniques involve simultaneously monitoring a wide depth of range across patient tissue structure. In some cases, opthalmological evaluation techniques as discussed herein can be used to obtain volumetric three dimensional images of the human eye. Exemplary techniques involve simultaneously monitoring multiple depth ranges with offsets, optionally with a single detector. Such approaches can ensure time coincidence and also lower hardware costs. In some cases, exemplary techniques do not involve the use of complicated IR detectors or swept light sources. In some cases, exemplary techniques do not involve the use of devices requiring a complex assembly of moving parts or complicated data acquisition and processing routines. According to some embodiments, angularly multiplexed signals from different depths or spatial locations can be combined on a single detector to provide simultaneous homodyne detection. According to some embodiments, such combination methods can provide a depth span for each angularly encoded signal, making it possible to simultaneously measure over a large effective depth of range or to simultaneously measure at different spatial locations.

In one aspect, embodiments of the present invention encompass angle multiplexed optical coherence tomography systems and methods for evaluating an eye of a patient. Exemplary systems include a light source, and an optical assembly for obtaining a plurality of sample beams corresponding to respective anatomical locations of the eye of the patient. Individual sample beams are associated with a respective angle relative to a reference beam. Systems can also include a detection mechanism that detects individual unique interference patterns respectively provided by the plurality of sample beams, for simultaneous evaluation of the anatomical locations. According to some embodiments, individual sample beams provide respective unique interference spatial periods at the detection mechanism. According to some embodiments, unique interference spatial periods are adjustable in response to changes in respective sample beam angles relative to the reference beam. In some cases, systems include one or more collimation lenses that direct combined sample-reference beam pairs toward the detection mechanism. In some cases, systems and methods provide an accuracy for range finding on the order of 10 microns. In some cases, systems include a filter assembly that transmits transmits interference signals at spatial frequencies about a first sample-reference beam pair and suppresses interference signals at spatial frequencies about a second sample-reference beam pair.

In another aspect, embodiments of the present invention encompass optical coherence tomography for evaluating an eye of a patient, which involve a light source, and an optical assembly for obtaining a sample beams corresponding to an anatomical location of the eye of the patient. The sample beam can be associated with an angle relative to a reference beam. Systems and methods can also involve a lens that receives the sample beam and reference beam as a pair of beams combined at the angle, and directs the combined sample-reference beam pair toward a detection mechanism that detects an interference pattern provided by the beam pair for evaluation of the anatomical location.

In another aspect, embodiments of the present invention encompass angle multiplexed optical coherence tomography systems and methods for evaluating an eye of a patient. Exemplary methods include obtaining a plurality of sample beams corresponding to respective anatomical locations of the eye of the patient. Individual sample beams can be associated with a respective angle relative to a reference beam. Methods may also include detecting individual unique interference patterns respectively provided by the plurality of sample beams, and evaluating the eye of the patient based on the detected interference patterns. In some cases, methods include positioning a corneal topography system relative to the eye based on the evaluation, and obtaining a corneal topography measurement of the eye. In some cases, topography measurements can be performed without aligning the corneal topography system using corneal topography fiducials.

DETAILED DESCRIPTION OF THE INVENTION

Figure 1:
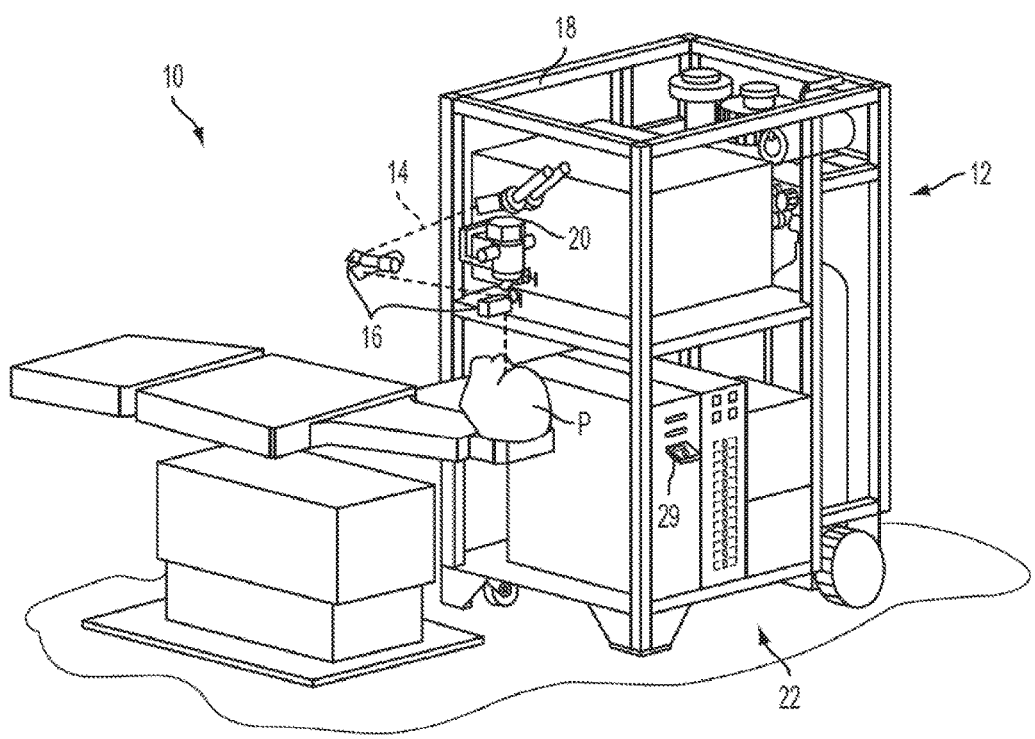
FIGS. 1 to 15 depict aspects of angular optical coherence tomography systems and methods according to embodiments of the present invention.

Embodiments of the present invention encompass systems and methods for the tomographical monitoring of optical or other patient tissue across a wide depth of range in a simultaneous fashion. According to some embodiments, angular multiplexed optical coherence tomography (AMOCT) techniques can use non-collinear beams to produce a spatial interference pattern with a unique carrier frequency. Such a frequency can be determined by the angle between the signal and reference beams. Multiple carrier frequencies can be supported simultaneously on a single linear array detector by assigning a unique angle to each unique signal beam and combining them with a single, common reference beam.

According to some embodiments, a detector can receive multiple signal frequencies simultaneously, and the readout of a signal assigned to a specific carrier frequency can be achieved by frequency filtering the composite signal. Having resolved the specific signals, the composite echo signal can be constructed using prior knowledge about their respective time delays or spatial locations. The delays in the various signals may be distributed to provide a large effective depth range useful in simultaneous anterior chamber depth (ACD), lens thickness, axial length, or other optical feature measurements. According to some embodiments, the signals may have similar delays but could sample various transverse locations simultaneously to provide multi-point measurements such as multipoint pachymetry without the need for moving parts.

Embodiments of the present invention can be readily adapted for use with existing laser systems and other optical diagnostic and treatment devices. Although system, software, and method embodiments of the present invention are described primarily in the context of a laser eye surgery system, it should be understood that embodiments of the present invention may be adapted for use in alternative eye diagnostic and treatment procedures, systems, or modalities, such as spectacle lenses, intraocular lenses, accommodating IOLs, contact lenses, corneal ring implants, collagenous corneal tissue thermal remodeling, corneal inlays, corneal onlays, other conical implants or grafts, and the like. Relatedly, systems, software, and methods according to embodiments of the present invention are well suited for customizing any of these treatment modalities to a specific patient. Thus, for example, embodiments encompass custom intraocular lenses, custom contact lenses, custom corneal implants, and the like, which can be configured to treat or ameliorate any of a variety of vision conditions in a particular patient based on their unique ocular characteristics or anatomy. Additionally, the ablation target or target shape may be implemented via other non-ablative laser therapies, such as laser-incised custom lenticule shapes and subsequent extraction and laser-based corneal incision patterns. Embodiments of the present invention are not limited to ophthalmic uses and can include analysis of translucent biological tissues and inorganic materials.

Turning now to the drawings, FIG. 1 illustrates a laser eye surgery system 10 of the present invention, including a laser 12 that produces a laser beam 14. Laser 12 is optically coupled to laser delivery optics 16, which directs laser beam 14 to an eye E of patient P. A delivery optics support structure (not shown here for clarity) extends from a frame 18 supporting laser 12. A microscope 20 is mounted on the delivery optics support structure, the microscope often being used to image a cornea of eye E.

Laser 12 generally comprises an excimer laser, ideally comprising an argon-fluorine laser producing pulses of laser light having a wavelength of approximately 193 nm. Laser 12 will preferably be designed to provide a feedback stabilized fluence at the patient's eye, delivered via delivery optics 16. The present invention may also be useful with alternative sources of ultraviolet or infrared radiation, particularly those adapted to controllably ablate the corneal tissue without causing significant damage to adjacent and/or underlying tissues of the eye. Such sources include, but are not limited to, solid state lasers and other devices which can generate energy in the ultraviolet wavelength between about 185 and 205 nm and/or those which utilize frequency-multiplying techniques. Hence, although an excimer laser is the illustrative source of an ablating beam, other lasers may be used in the present invention.

Laser system 10 will generally include a computer or programmable processor 22. Processor 22 may comprise (or interface with) a conventional PC system including the standard user interface devices such as a keyboard, a display monitor, and the like. Processor 22 will typically include an input device such as a magnetic or optical disk drive, an internet connection, or the like. Such input devices will often be used to download a computer executable code from a tangible storage media 29 embodying any of the methods of the present invention. Tangible storage media 29 may take the form of a floppy disk, an optical disk, a data tape, a volatile or non-volatile memory, RAM, or the like, and the processor 22 will include the memory boards and other standard components of modern computer systems for storing and executing this code. Tangible storage media 29 may optionally embody wavefront sensor data, wavefront gradients, a wavefront elevation map, a treatment map, a corneal elevation map, and/or an ablation table. While tangible storage media 29 will often be used directly in cooperation with a input device of processor 22, the storage media may also be remotely operatively coupled with processor by means of network connections such as the internet, and by wireless methods such as infrared, Bluetooth, or the like.

Laser 12 and delivery optics 16 will generally direct laser beam 14 to the eye of patient P under the direction of a computer 22. Computer 22 will often selectively adjust laser beam 14 to expose portions of the cornea to the pulses of laser energy so as to effect a predetermined sculpting of the cornea and alter the refractive characteristics of the eye. In many embodiments, both laser beam 14 and the laser delivery optical system 16 will be under computer control of processor 22 to effect the desired laser sculpting process, with the processor effecting (and optionally modifying) the pattern of laser pulses. The pattern of pulses may by summarized in machine readable data of tangible storage media 29 in the form of a treatment table, and the treatment table may be adjusted according to feedback input into processor 22 from an automated image analysis system in response to feedback data provided from an ablation monitoring system feedback system. Optionally, the feedback may be manually entered into the processor by a system operator. Such feedback might be provided by integrating the wavefront measurement system described below with the laser treatment system 10, and processor 22 may continue and/or terminate a sculpting treatment in response to the feedback, and may optionally also modify the planned sculpting based at least in part on the feedback. Measurement systems are further described in U.S. Pat. No. 6,315, 413, the full disclosure of which is incorporated herein by reference.

Laser beam 14 may be adjusted to produce the desired sculpting using a variety of alternative mechanisms. The laser beam 14 may be selectively limited using one or more variable apertures. An exemplary variable aperture system having a variable iris and a variable width slit is described in U.S. Pat. No. 5,713,892, the full disclosure of which is incorporated herein by reference. The laser beam may also be tailored by varying the size and offset of the laser spot from an axis of the eye, as described in U.S. Pat. Nos. 5,683,379, 6,203,539, and 6,331,177, the full disclosures of which are incorporated herein by reference.

Still further alternatives are possible, including scanning of the laser beam over the surface of the eye and controlling the number of pulses and/or dwell time at each location, as described, for example, by U.S. Pat. No. 4,665,913, the full disclosure of which is incorporated herein by reference; using masks in the optical path of laser beam 14 which ablate to vary the profile of the beam incident on the cornea, as described in U.S. Pat. No. 5,807,379, the full disclosure of which is incorporated herein by reference; hybrid profile-scanning systems in which a variable size beam (typically controlled by a variable width slit and/or variable diameter iris diaphragm) is scanned across the cornea; or the like. The computer programs and control methodology for these laser pattern tailoring techniques are well described in the patent literature.

Additional components and subsystems may be included with laser system 10, as should be understood by those of skill in the art. For example, spatial and/or temporal integrators may be included to control the distribution of energy within the laser beam, as described in U.S. Pat. No. 5,646, 791, the full disclosure of which is incorporated herein by reference. Ablation effluent evacuators/filters, aspirators, and other ancillary components of the laser surgery system are known in the art. Further details of suitable systems for performing a laser ablation procedure can be found in commonly assigned U.S. Pat. Nos. 4,665,913, 4,669,466, 4,732,148, 4,770,172, 4,773,414, 5,207,668, 5,108,388, 5,219,343, 5,646,791 and 5,163,934, the complete disclosures of which are incorporated herein by reference. Suitable systems also include commercially available refractive laser systems such as those manufactured and/or sold by Alcon, Bausch & Lomb, Nidek, WaveLight, LaserSight, Schwind, Zeiss-Meditec, and the like. Basis data can be further characterized for particular lasers or operating conditions, by taking into account localized environmental variables such as temperature, humidity, airflow, and aspiration.

Figure 2:
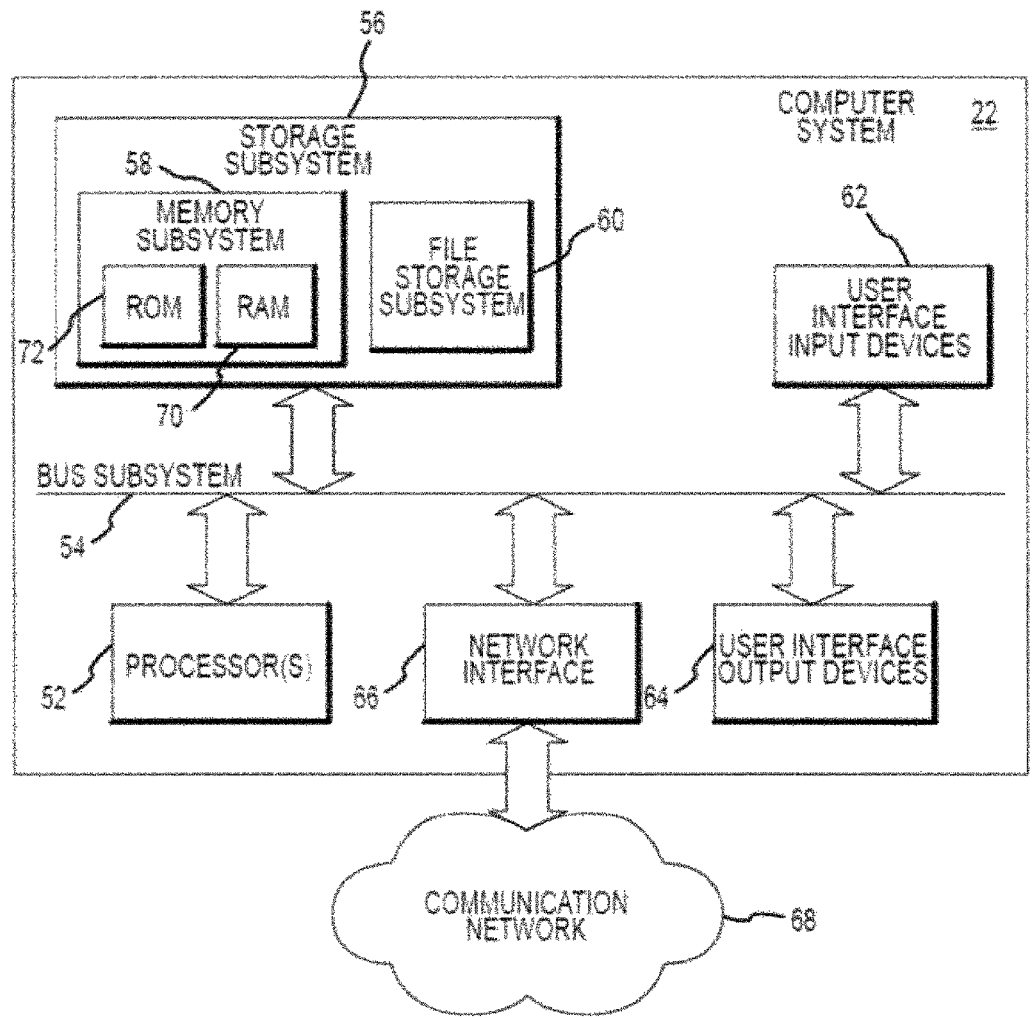

FIG. 2 is a simplified block diagram of an exemplary computer system 22 that may be used by the laser surgical system 10 of the present invention. Computer system 22 typically includes at least one processor 52 which may communicate with a number of peripheral devices via a bus subsystem 54. These peripheral devices may include a storage subsystem 56, comprising a memory subsystem 58 and a file storage subsystem 60, user interface input devices 62, user interface output devices 64, and a network interface subsystem 66. Network interface subsystem 66 provides an interface to outside networks 68 and/or other devices, such as the wavefront measurement system 30.

User interface input devices 62 may include a keyboard, pointing devices such as a mouse, trackball, touch pad, or graphics tablet, a scanner, foot pedals, a joystick, a touch-screen incorporated into the display, audio input devices such as voice recognition systems, microphones, and other types of input devices. User input devices 62 will often be used to download a computer executable code from a tangible storage media 29 embodying any of the methods of the present invention. In general, use of the term "input device" is intended to include a variety of conventional and proprietary devices and ways to input information into computer system 22.

User interface output devices 64 may include a display subsystem, a printer, a fax machine, or non-visual displays such as audio output devices. The display subsystem may be a cathode ray tube (CRT), a flat-panel device such as a liquid crystal display (LCD), a projection device, or the like. The display subsystem may also provide a non-visual display such as via audio output devices. In general, use of the term "output device" is intended to include a variety of conventional and proprietary devices and ways to output information from computer system 22 to a user.

Storage subsystem 56 can store the basic programming and data constructs that provide the functionality of the various embodiments of the present invention. For example, a database and modules implementing the functionality of the methods of the present invention, as described herein, may be stored in storage subsystem 56. These software modules are generally executed by processor 52. In a distributed environment, the software modules may be stored on a plurality of computer systems and executed by processors of the plurality of computer systems. Storage subsystem 56 typically comprises memory subsystem 58 and file storage subsystem 60.

Memory subsystem 58 typically includes a number of memories including a main random access memory (RAM) 70 for storage of instructions and data during program execution and a read only memory (ROM) 72 in which fixed instructions are stored. File storage subsystem 60 provides persistent (non-volatile) storage for program and data files, and may include tangible storage media 29 (FIG. 1) which may optionally embody wavefront sensor data, wavefront gradients, a wavefront elevation map, a treatment map, and/or an ablation table. File storage subsystem 60 may include a hard disk drive, a floppy disk drive along with associated removable media, a Compact Digital Read Only Memory (CD-ROM) drive, an optical drive, DVD, CD-R, CD-RW, solid-state removable memory, and/or other removable media cartridges or disks. One or more of the drives may be located at remote locations on other connected computers at other sites coupled to computer system 22. The modules implementing the functionality of the present invention may be stored by file storage subsystem 60.

Bus subsystem 54 provides a mechanism for letting the various components and subsystems of computer system 22 communicate with each other as intended. The various subsystems and components of computer system 22 need not be at the same physical location but may be distributed at various locations within a distributed network. Although bus subsystem 54 is shown schematically as a single bus, alternate embodiments of the bus subsystem may utilize multiple busses.

Computer system 22 itself can be of varying types including a personal computer, a portable computer, a workstation, a computer terminal, a network computer, a control system in a wavefront measurement system or laser surgical system, a mainframe, or any other data processing system. Due to the ever-changing nature of computers and networks, the description of computer system 22 depicted in FIG. 2 is intended only as a specific example for purposes of illustrating one embodiment of the present invention. Many other configurations of computer system 22 are possible having more or less components than the computer system depicted in FIG. 2.

Figure 3:
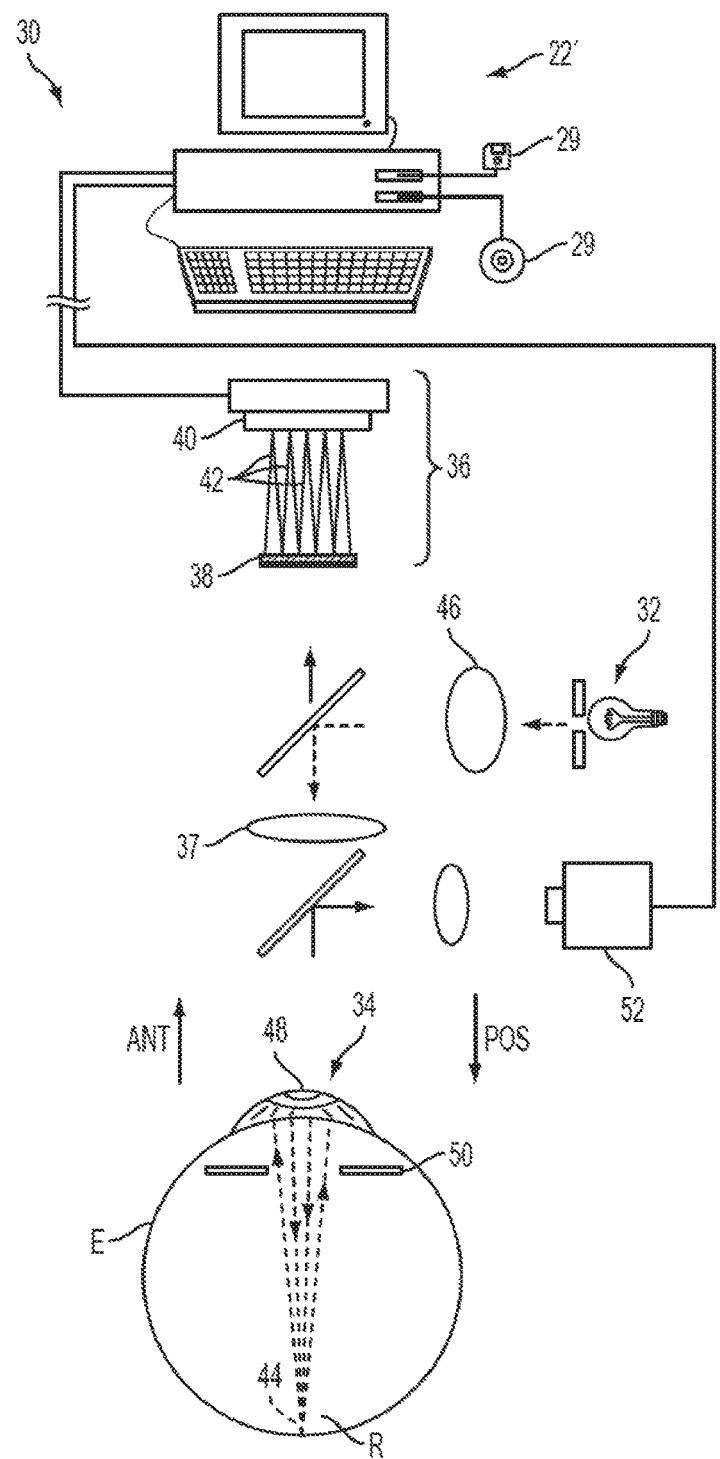

Referring now to FIG. 3, one embodiment of a wavefront measurement system 30 is schematically illustrated in simplified form. In very general terms, wavefront measurement system 30 is configured to sense local slopes of a gradient map exiting the patient's eye. Devices based on the Hartmann-Shack principle generally include a lenslet array to sample the gradient map uniformly over an aperture, which is typically the exit pupil of the eye. Thereafter, the local slopes of the gradient map are analyzed so as to reconstruct the wavefront surface or map.

More specifically, one wavefront measurement system 30 includes an image source 32, such as a laser, which projects a source image through optical tissues 34 of eye E so as to form an image 44 upon a surface of retina R. The image from retina R is transmitted by the optical system of the eye (e.g., optical tissues 34) and imaged onto a wavefront sensor 36 by system optics 37. The wavefront sensor 36 communicates signals to a computer system 22' for measurement of the optical errors in the optical tissues 34 and/or determination of an optical tissue ablation treatment program. Computer 22' may include the same or similar hardware as the computer system 22 illustrated in FIGS. 1 and 2. Computer system 22' may be in communication with computer system 22 that directs the laser surgery system 10, or some or all of the components of computer system 22, 22' of the wavefront measurement system 30 and laser surgery system 10 may be combined or separate. If desired, data from wavefront sensor 36 may be transmitted to a laser computer system 22 via tangible media 29, via an I/O port, via an networking connection 66 such as an intranet or the Internet, or the like.

Wavefront sensor 36 generally comprises a lenslet array 38 and an image sensor 40. As the image from retina R is transmitted through optical tissues 34 and imaged onto a surface of image sensor 40 and an image of the eye pupil P is similarly imaged onto a surface of lenslet array 38, the lenslet array separates the transmitted image into an array of beamlets 42, and (in combination with other optical components of the system) images the separated beamlets on the surface of sensor 40. Sensor 40 typically comprises a charged couple device or "CCD," and senses the characteristics of these individual beamlets, which can be used to determine the characteristics of an associated region of optical tissues 34. In particular, where image 44 comprises a point or small spot of light, a location of the transmitted spot as imaged by a beamlet can directly indicate a local gradient of the associated region of optical tissue.

Eye E generally defines an anterior orientation ANT and a posterior orientation POS. Image source 32 generally projects an image in a posterior orientation through optical tissues 34 onto retina R as indicated in FIG. 3. Optical tissues 34 again transmit image 44 from the retina anteriorly toward wavefront sensor 36. Image 44 actually formed on retina R may be distorted by any imperfections in the eye's optical system when the image source is originally transmitted by optical tissues 34. Optionally, image source projection optics 46 may be configured or adapted to decrease any distortion of image 44.

In some embodiments, image source optics 46 may decrease lower order optical errors by compensating for spherical and/or cylindrical errors of optical tissues 34. Higher order optical errors of the optical tissues may also be compensated through the use of an adaptive optic element, such as a deformable mirror (described below). Use of an image source 32 selected to define a point or small spot at image 44 upon retina R may facilitate the analysis of the data provided by wavefront sensor 36. Distortion of image 44 may be limited by transmitting a source image through a central region 48 of optical tissues 34 which is smaller than a pupil 50, as the central portion of the pupil may be less prone to optical errors than the peripheral portion. Regardless of the particular image source structure, it will be generally be beneficial to have a well-defined and accurately formed image 44 on retina R.

In one embodiment, the wavefront data may be stored in a computer readable medium 29 or a memory of the wavefront sensor system 30 in two separate arrays containing the x and y wavefront gradient values obtained from image spot analysis of the Hartmann-Shack sensor images, plus the x and y pupil center offsets from the nominal center of the Hartmann-Shack lenslet array, as measured by the pupil camera 51 (FIG. 3) image. Such information contains all the available information on the wavefront error of the eye and is sufficient to reconstruct the wavefront or any portion of it. In such embodiments, there is no need to reprocess the Hartmann-Shack image more than once, and the data space required to store the gradient array is not large. For example, to accommodate an image of a pupil with an 8 mm diameter, an array of a 20×20 size (i.e., 400 elements) is often sufficient. As can be appreciated, in other embodiments, the wavefront data may be stored in a memory of the wavefront sensor system in a single array or multiple arrays.

While the methods of the present invention will generally be described with reference to sensing of an image 44, a series of wavefront sensor data readings may be taken. For example, a time series of wavefront data readings may help to provide a more accurate overall determination of the ocular tissue aberrations. As the ocular tissues can vary in shape over a brief period of time, a plurality of temporally separated wavefront sensor measurements can avoid relying on a single snapshot of the optical characteristics as the basis for a refractive correcting procedure. Still further alternatives are also available, including taking wavefront sensor data of the eye with the eye in differing configurations, positions, and/or orientations. For example, a patient will often help maintain alignment of the eye with wavefront measurement system 30 by focusing on a fixation target, as described in U.S. Pat. No. 6,004,313, the full disclosure of which is incorporated herein by reference. By varying a position of the fixation target as described in that reference, optical characteristics of the eye may be determined while the eye accommodates or adapts to image a field of view at a varying distance and/or angles.

The location of the optical axis of the eye may be verified by reference to the data provided from a pupil camera 52. In the exemplary embodiment, a pupil camera 52 images pupil 50 so as to determine a position of the pupil for registration of the wavefront sensor data relative to the optical tissues.

Figure 3A:
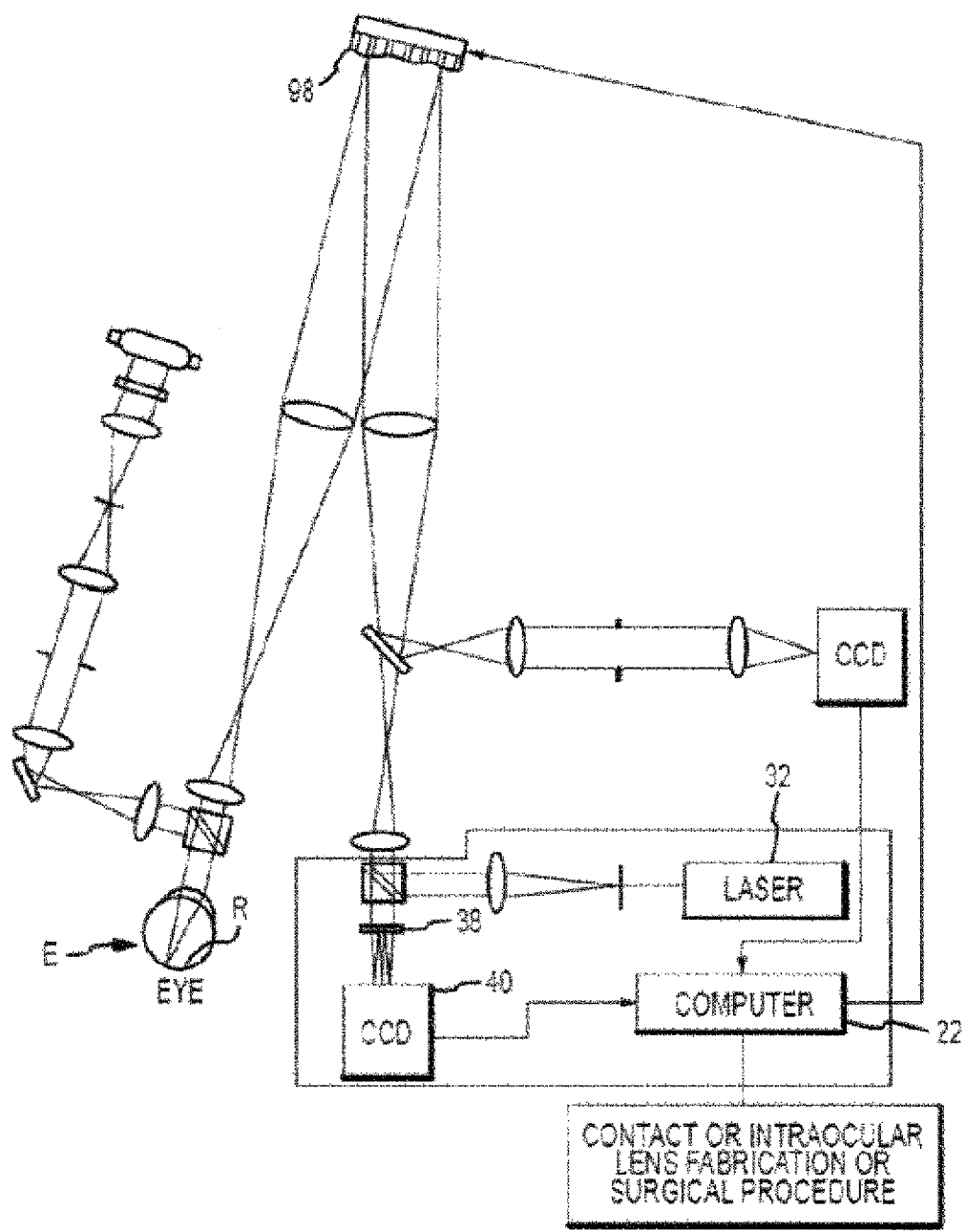

An alternative embodiment of a wavefront measurement system is illustrated in FIG. 3A. The major components of the system of FIG. 3A are similar to those of FIG. 3. Additionally, FIG. 3A includes an adaptive optical element 53 in the form of a deformable mirror. The source image is reflected from deformable mirror 98 during transmission to retina R, and the deformable mirror is also along the optical path used to form the transmitted image between retina R and imaging sensor 40. Deformable mirror 98 can be controllably deformed by computer system 22 to limit distortion of the image formed on the retina or of subsequent images formed of the images formed on the retina, and may enhance the accuracy of the resultant wavefront data. The structure and use of the system of FIG. 3A are more fully described in U.S. Pat. No. 6,095,651, the full disclosure of which is incorporated herein by reference.

The components of an embodiment of a wavefront measurement system for measuring the eye and ablations may comprise elements of a WaveScan® system, available from AMO MANUFACTURING USA, LLC, MILPITAS, Calif. One embodiment includes a WaveScan system with a deformable mirror as described above. An alternate embodiment of a wavefront measuring system is described in U.S. Pat. No. 6,271,915, the full disclosure of which is incorporated herein by reference. It is appreciated that any wavefront aberrometer could be employed for use with the present invention. Relatedly, embodiments of the present invention encompass the implementation of any of a variety of optical instruments provided by AMO WaveFront Sciences, LLC, including the COAS wavefront aberrometer, the ClearWave contact lens aberrometer, the CrystalWave IOL aberrometer, and the like.

Relatedly, embodiments of the present invention encompass the implementation of any of a variety of optical instruments provided by WaveFront Sciences, Inc., including the COAS wavefront aberrometer, the ClearWave contact lens aberrometer, the CrystalWave IOL aberrometer, and the like. Embodiments of the present invention may also involve wavefront measurement schemes such as a Tscherning-based system, which may be provided by WaveFront Sciences, Inc. Embodiments of the present invention may also involve wavefront measurement schemes such as a ray tracing-based system, which may be provided by Tracey Technologies, Corp.

Optical Coherence Tomography (OCT)

Optical coherence tomography (OCT) system and methods may be used to ascertain the location and orientation of the anatomical features within the eye (e.g., the anterior and posterior corneal surfaces, capsular bag, lens, and the like), either prior to, during, or after a surgical procedure. These data can be used to advantage in planning the surgical treatment. For example, in advanced LASIK planning, the location of the critical refractive surfaces, in conjuction with wavefront data, can be used to customize the corneal ablastion. See, e.g., Mrochen et al., "*Optical ray tracing for the calculation of optimized corneal ablation profiles in refractive treatment planning*" J. Refract. Surg., April, 24(4): S446-S451 (2008), the content of which is incorporated herein by reference. In some cases, such evaluation techniques can be performed in combination with a femtosecond laser treatment to create incisions within corneal tissue to form a LASIK flap. Other ophthalmic treatments involve procedures performed on anatomical features within the eye, such as the capsular bag, lens, cornea, and the like. Such treatments may involve the removal of cataracts. Embodiments of the present invention encompass methods and systems for analyzing the ophthalmic anatomy of a patient via certain OCT techniques, and/or for providing therapeutic treatment to the ophthalmic anatomy. In some cases, techniques may involve evaluating an ophthalmic anatomical feature of the eye, and optionally operating a laser beam or providing some other therapeutic treatment modality to one or more of the anatomical features. Exemplary therapeutic treatments (e.g. which may be performed with a femtosecond laser or other device) include phacoemulsification, capsulorhexis, capsulotomy, and the like. Capsulotomy procedures generally refer to procedure where the capsule is removed. Capsulorhexis procedures involve cutting of capsule and phacoemulsification procedures involve disrupting, breaking up, or emulsifying the lens. Such treatments may be performed as part of an extracapsular cataract extraction procedure (ECCE).

Embodiments of the present invention can be readily adapted for use with existing laser systems and other optical treatment devices. Although system, software, and method embodiments of the present invention are described primarily in the context of a laser eye surgery system, it should be understood that embodiments of the present invention may be adapted for use in alternative eye treatment procedures, systems, or modalities, such as spectacle lenses, intraocular lenses, accommodating IOLs, contact lenses, corneal ring implants, collagenous corneal tissue thermal remodeling, conical inlays, conical onlays, other corneal implants or grafts, and the like. Relatedly, systems, software, and methods according to embodiments of the present invention are well suited for customizing any of these treatment modalities to a specific patient. Thus, for example, embodiments encompass custom intraocular lenses, custom contact lenses, custom corneal implants, and the like, which can be configured to treat or ameliorate any of a variety of vision conditions in a particular patient based on their unique ocular characteristics or anatomy.

A wide variety of OCT devices (eg., spectral domain (SDOCT), swept source (SSOCT), time domain (TDOCT)) have been proposed, often involving white light interferometers incorporating a light source that has wide spectral width or which can be tuned rapidly over wide spectral range. A useful review of OCT methods can be found in Wojtkowski, "*High-speed optical coherence tomography: basics and applications*" Appl. Opt., June 1, 49(16):D30-61 (2010), the content of which is incorporated herein by reference. Typically, the light is split into two components, one of which serves as a reference and the other to probe the sample in question. The beams are recombined and produce an interference pattern which is detected and analyzed to deduce range information. The interference pattern is produced when the recombined beams have a path length difference within the coherence length of the light source. Indeed this is what determines the depth resolution of the OCT system. In such cases of OCT, the depth resolution is determined by the effective spectral breadth of the light source according to the following equation.

$$L_c = \frac{2\ln(2)}{\pi n} \frac{\lambda}{\Delta\lambda} \lambda$$

where
n=refractive index
λ=center wavelength
Δλ=spectral width (FWHM)

A super luminescent diode is often used to provide a wide spectral width having good transverse coherence. In the case of SSOCT, the effective spectral breadth is given by the tuning range of the swept source. The interference pattern can be detected in a number of ways. In SDOCT, the interference is imposed as a modulation in the spectrum of the combined return light and is detected by using spectrometer. In SSOCT, a narrow bandwidth source is tuned and the interference is imposed as a time modulation on the combined return light and is detected with a balanced photodiode. Likewise, the interference is a time modulation in TDOCT where the interference is created by varying the reference path length.

The depth range of the OCT systems can also depend on the OCT type. For SDOCT, the depth range is limited by the spectral resolution of the spectrometer to a few millimeters. SSOCT systems have depth range that is either limited by the k-frequency sample rate of the interference signal, or by the bandwidth of the narrow bandwidth laser source according to the equation above, whichever is shorter. TDOCT has an advantage over most other OCT systems in that the depth range is limited only by the range over which the reference leg is varied; indeed, commercial devices using this method have been available for biometry of the eye; unfortunately, the required large motion of the reference path can introduce sufficient time for variations in the sample path due to eye motion, thus compromising the integrity of the measurement. Only recently, through the use of specialized MEMS tunable vertical-cavity surface emitting laser with long coherence length and a high speed digitization circuit, has a depth range of tens of millimeters been attained in combination with high speed OCT acquisition. Use of such OCT systems has finally allowed full eye OCT imaging. See, e.g., Grulkowski et al., "*Retinal, anterior segment and full eye imaging using ultrahigh speed swept source OCT with vertical-cavity surface emitting lasers*", Biomedical Optics Express, November, 3(11):2733-51 (2012), the content of which is incorporated herein by reference. Knupfer and Hauger have described an OCT method comprised of two beams combined noncolinearly on a detector in U.S. Pat. No. 6,396,587, the content of which is incorporated herein by reference. Like many other OCT systems the broadband source is split into reference and signal beams. The reference and return signal beams are contained in optical fibers. These optical fibers are simply directed toward a detector having a multiplicity of pixels distributed in the plane containing both fibers. The light emitted from the fibers produces a spatially compact interference pattern modulated across the detector. The pattern is displaced along the detector according the path length difference between the reference and return signal beams. Related systems are described in Hauger et al., "Interferometer for Optical Coherence Tomography", Applied Optics, Vol. 42 Issue 19, pp. 3896-3902 (2003), the content of which is incorporated herein by reference. It is noted that such systems involve non-linear displacement in the path difference.

Angle Multiplexed Optical Coherence Tomography (AMOCT)

As discussed elsewhere herein, angle multiplexed optical coherence tomography (AMOCT) systems and methods can involve the use of multiple test beams (optionally, with differing delays) which can be combined with a single reference beam on a single detector, for purposes of evaluating the ocular anatomy of an individual patient. Embodiments disclosed herein involve the use of optics to linearize the interference pattern displacement with path difference and the combination of multiple signal beams to provide simultaneous OCT measurements. According to some embodiments, individual test beams can be assigned respective unique spatial frequencies. For example, it is possible to assign or correlate an individual test beam to a unique angle relative to the reference beam. According to some embodiments, individual spatial frequencies can be resolved from the detector signal using Fourier analysis with matched filters, in a manner similar to how a radio operates to isolate individual stations. Accordingly, AMOCT can involve the simultaneous measurement of multiple test beams. According to some embodiments, where a return beam is weak compared to a reference beam, the fringes due to the signal beam interference are very weak and are at a different spatial frequency. According to some embodiments, return return beams can be collected on multiple fibers, probing different spatial or depth regions.

Figure 5:
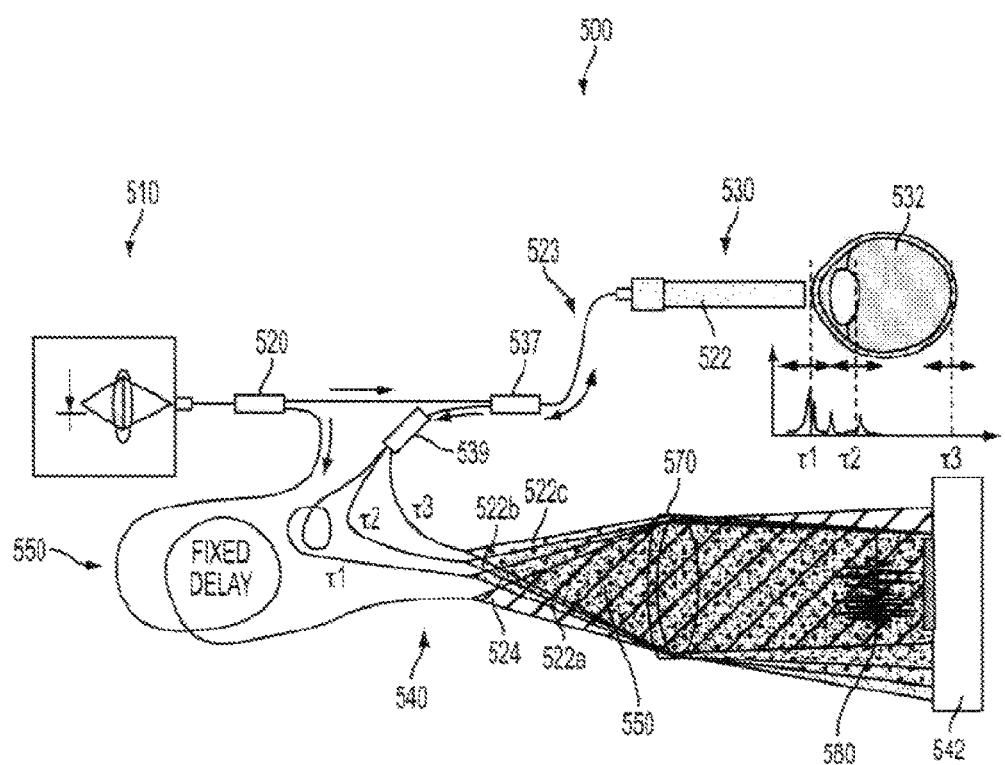

An analysis of multiple beam interference that follows includes n collimated beams propagating in different directions, $k_j$. As depicted in FIG. 5, multiple beams can be combined through a single collimating lens on a single detector, though multiple collimation lenses could be used. This analysis yields the following equation for the detected spatial intensity of the combined beams:

$$I(\omega, \vec{r}) = \sum_j |E_j(\omega)|^2 + \frac{1}{2}\sum_{j \ne l} \left\{ E_j(\omega)E_l^*(\omega)e^{-i\left[(\hat{k}_j - \hat{k}_l)\cdot\vec{r}\frac{\omega}{c} + (\phi_j - \phi_l)\right]} + E_l(\omega)E_j^*(\omega)e^{-i\left[(\hat{k}_j - \hat{k}_l)\cdot\vec{r}\frac{\omega}{c} + (\phi_j - \phi_l)\right]} \right\}$$

where $E_j$ and ω are the electric field amplitude and the frequency of each beam, respectively, and c is the speed of light. The first term is the incoherent sum of the beam intensities and the second term contains is the interferences between each beams. This equation is further simplified with a few definitions $$I(\omega, \vec{r}) = \sum_j I_j(\omega) + \sum_{j \ne l} \sqrt{I_j(\omega)I_l(\omega)} \cos\left[\left(\frac{\Delta\vec{k}_{jl}\cdot\vec{r}}{c} + \tau_{jl}\right)\omega\right]$$

where
$I_j(\omega) = |E_j(\omega)|^2$ $\Delta\vec{k}_{jl} = \hat{k}_j - \hat{k}_l$ $\tau_{jl}\omega = \phi_j - \phi_l$ The intensity of each beam is given by $I_j(\omega)$, $\Delta k_{jl}$ is the difference in propagation directions of each pair of beams, and $\tau_{jl}$ is the path delay difference (in units of time). This equation may be relevant to various OCT methods.

For the collinear methods of SDOCT, SSOCT and TDOCT, $\Delta k_{jl}$ equals 0 leaving $$I(\omega) = \sum_j I_j(\omega) + \sum_{j\neq l} \sqrt{I_j(\omega)I_l(\omega)} \cos[\tau_{jl}\omega]$$

The OCT signal for SDOCT is the spectrally resolved I($\omega$), SSOCT contains an implicit time dependence in $\omega(t)$ as the laser frequency is tuned yielding a time dependent signal, I(t). Finally, TDOCT contains a variable $\tau_{jl}$ as the reference path length is varied in time; in this case the detector integrates over all frequencies $\omega$. In each case, the modulation depth of interference is twice the square root of the product of intensities.

The above equation involves a notable short coming of collinear OCT methods—that the signals due to positive and negative delays are not distinguishable. Indeed to distinguish between positive and negative delays, some have proposed phase shift detection methods such as that noted by Wotjkowski et al., "Full range complex spectral optical coherence tomography technique in eye imaging" Optics Letters, Vol. 27, Issue 16, pp. 1415-1417 (2002), the content of which is incorporated herein by reference. Such methods use weighted averages of five OCT images with phase shifts in the reference path length. While improving the depth range and signal to noise ratio of these OCT methods, this technique has the drawbacks of requiring a precise phase shift mechanism like a piezoelectric tranducer, a stable path length to the sample, and reduces the overall acquisition rate by a factor of five.

Now consider the non-colinear case. Assuming without loss of generality, that the beams propagate in the xz plane of our coordinate system, that the reference beam (the $l^{th}$ beam) propagates along the z axis and the $j^{th}$ beam propagates at an angle $\theta_{jl}$ with respect to the z axis, that the detector is located at z=0 and oriented along the x direction and then the OCT equation equation simplifies. Note that like the TDOCT case, the detector integrates over all frequencies yielding $$I(x) = \int \sum_j I_j(\omega) + \sum_{j\neq l} \sqrt{I_j(\omega)I_l(\omega)} \cos\left[\left(\frac{x\sin[\theta]_{jl}}{c} + \tau_{jl}\right)\omega\right] d\omega$$

The OCT signal is dependent on detector position, x, which acts like a scaled version of the time delay, $\tau_{jl}$. The x position represents a true linear time delay induced by the non-colinearity of the beams without the sign ambiguity of other OCT methods. The spatial period of the interference signal produced by the $j^{th}$ and $l^{th}$ beams is given by $$\text{Period}_{jl} = \frac{\omega\sin[\theta_{jl}]}{c} = \frac{2\pi}{\lambda}\sin[\theta_{jl}]$$

where $\lambda$ is the wavelength of the source. Thus we see that each pair of beams produces an interference signal with unique spatial period. There is a unique period adjustable by angle of propagation. Multiple beams can be combined on a single detector, each pair of which produce an OCT interference that can be separated from the others by virtue of its unique spatial period. In the case of a narrowband source, the interference signal extends across the detector; however, if the source has sufficient bandwidth, then the interference signal is localized about the point where the reference and signal beam delays are equal with an extent determined by the source coherence length.

According to some embodiments, AMOCT systems and methods may involve combining a reference beam with the test beam at an angle to produce spatial interference fringes. In some instances, a maximum range can be obtained when the spatial period is just resolved by the detector. In some instances, if one fringe covers 4 pixels, then 4 pixels equal one wave ($\lambda$) of optical delay. In some instances, if the number of detectors is N, then the useful AMOCT z range is N*$\lambda$/4. According to some embodiments, AMOCT can use a simple broadband source, such as an SLD. According to some AMOCT embodiments, the width of the fringe envelope can be inversely related to the bandwidth of the source. According to some embodiments, AMOCT systems and methods may involve monitoring multiple beams. According to some embodiments, AMOCT systems and methods may involve the use of an optical delay that is rigorously linear in the detector position. According to some embodiments, AMOCT systems and methods may operate with no ambiguity with regard to positive and negative relative delays.

OCT embodiments of the instant invention can be used to provide highly precise rangefinder limits which enable extremely accurate elevation map evaluations. For example, certain OCT techniques can provide an accuracy for range finding on the order of 10 microns, and thus provide improved standards of precision for corneal topography evaluations. In some cases, the incorporation of selected OCT techniques can eliminate or reduce the need for corneal topography fiducials during alignment by providing accurate feedback to position optical equipment. As discussed elsewhere here, OCT embodiments can be used to characterize aspects of the corneal and other optical features, as well as other tissues. Corneal thickness (pachymetry) is a useful screening parameter to qualify patients for LASIK and other surgeries, and OCT approaches as discussed herein can enhance such measurements. Further, selected OCT techniques can be used to supplement or provide improved biometric measurements of corneal stiffness (e.g., tonography). In some cases, the OCT systems and methods discussed herein can be used in ocular biometry for advanced LASIK treatment planning and IOL fitting. Exemplary OCT techniques can be used to measure anterior chamber depth, lens thickness, axial length, and other anatomical features of the eye. Further, exemplary OCT measurements can be combined with tomographic wavefront measurements and Purkinge data to model or evaluate individual eyes comprehensively.

Embodiments of the present invention provide OCT techniques where the optical range is not limited by the resolution of the spectrometer or detector, and where positive and negative displacements are distinguishable with single measurements. Further, embodiments provide OCT techniques where the optical range is not limited by the detector bandwidth, and where higher detector bandwidths can be used without a corresponding increase in noise levels. What is more, embodiments of the present invention provide OCT techniques where sensitivity is retained at the extremes of the optical range, and where OCT signals with different depth offsets can be measured simultaneously.

Single Signal-Reference Beam Pair

Figure 4:
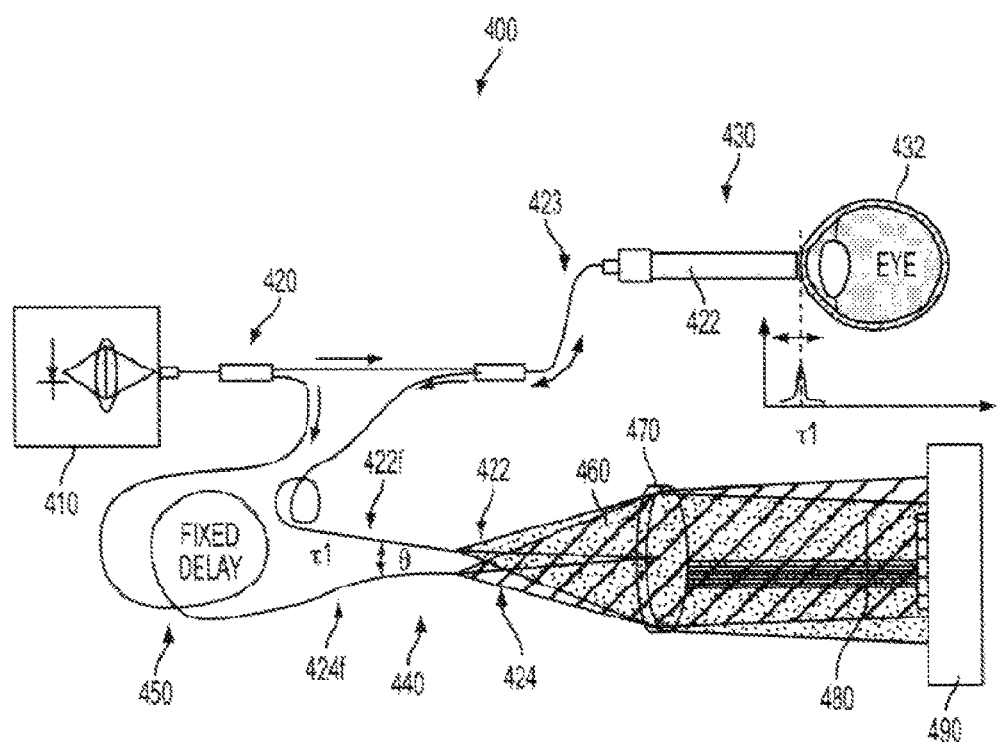
Figure 8:
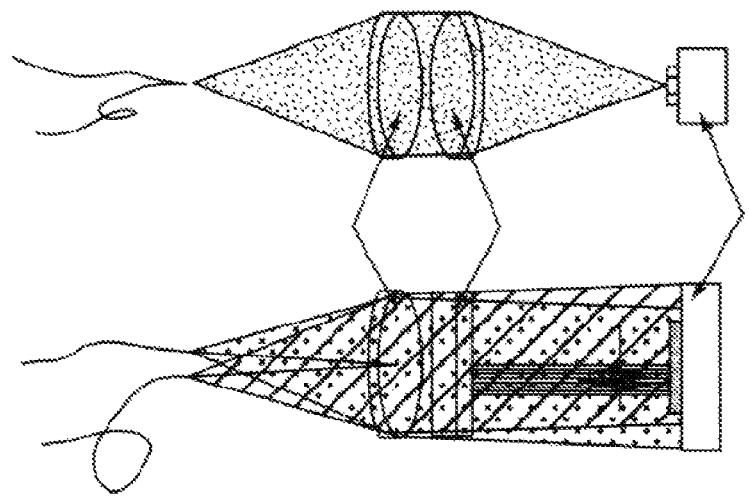

FIG. 4 illustrates aspects of angular multiplexed optical coherence tomography (AMOCT) systems and methods according to embodiments of the present invention. As depicted here, the AMOCT system 400 includes a light source 410. The light source may be provided as a single source light mechanism, such as a super luminescent diode (SLD), which may be fiber-coupled. In some cases, light from the light source can be coupled into a fiber and split into two beams by a fiber coupler. As shown here, a fiber splitter 420 can be used to direct a signal or sample beam along a sample leg 430 toward a test object 432 (such as an eye) and a reference beam along a reference leg 440 toward a detector 442 such as an array detector. Here, the reference beam is delayed by running the reference beam through a delay mechanism 450. For example, the reference beam can be delayed a fixed amount by running the beam through additional fiber length and/or free space. The signal beam 422 is retro-reflected from the test object 432 and re-injected into its fiber 423. As shown here, the reference beam 424 is not retro-reflected through its fiber nor is it recombined collinearly with the signal beam in the splitter. Rather, the reference beam is combined non-collinearly with the retro-reflected signal beam in free space at location 460. The signal beam 422 light and the reference beam 424 light from their respective fibers 422f, 424f are combined on a lens 470. As shown here, the lens 470 can provide a collimating function. Hence, the signal and reference beams eminating from their respective optical fibers can be collimated by the lens. The wavefront from each of the diverging beams can be considered as a non-planar wavefront (e.g. spherical). By incorporating the collimating lens 470, it is possible to achieve a linear relationship between movement of the object 432 (e.g. eye) corresponding to the sample leg and movement of the fringe pattern on the array detector 490. For example, the linear relationship can be provided in a 1:1 ratio. That is, movement of the object results in a corresponding linear movement of the fringe pattern. The beat note or spatial period of the fringe pattern 480 can be determined by the angle θ between the combined signal and reference beams. By implementing the lens 470, it is possible to obtain a constant interference period across the array detector, regardless of the position of the fringe pattern on the detector. Hence, the location of the fringe pattern is accurate and the resolution device is precise, at least partially as a result of the lens. As shown in FIG. 8, various lens configurations may be used.

With returning reference to FIG. 4, it can be seen that various time delays may be implemented in the system. The interoferometric aspects of OCT techniques can depend on path differences between reference leg light and sample leg light. Such differences can be expressed in terms of time (e.g. delays) or distance (e.g. length). According to some embodiments, where differences in time are discussed, it is also understood that differences in length may be similar. For example, individual optical fibers having different lengths may provide different amounts of time delay due to the difference in propagation duration. Typically, OCT operates where there is little or no time delay or difference in distance between sample and reference beams. For example, OCT may operate where the difference is within a range of a few millimeters. As shown here, τ1 may refer to a fixed time delay. According to some embodiments, the reference leg involves a fixed delay, and the sample leg involves a variable delay. In some cases, a sample leg may involve a variable delay in addition to a fixed delay). In some cases, the τ1 delay on the sample leg fiber depicted here is fixed.

A fixed delay may be provided by a length of fiber and/or an air path, which provide no change. According to some embodiments, a localized fringe pattern 480 is obtained when the net delay on the reference leg is the same or substantially the same as the net delay on the sample leg. Hence, a fringe pattern may result from a narrow region or band of delay at or near that equality (e.g. net sample leg delay=net reference leg delay). According to some embodiments, a broadband light source is used for OCT, and the light coherently interferes over a distance that is equal to the coherence length. A large bandwidth may correspond to a short coherence length. According to some embodiments, the depth resolution may be determined by or dependent on the bandwidth of the light source. According to some embodiments, a fringe pattern is produced with the delay amount is within the coherence length of the light source. Hence, for example, a fringe pattern may appear within a 10 micron band (e.g. plus or minus 5 microns relative to a fixed reference leg delay). Where a short coherence length light source is used (e.g. wide or large bandwidth), the fringe pattern may be limited to a narrow configuration that can be conveniently localized on a detector. In this sense, where one signal beam and one reference beam are used, the configuration can be considered to provide a single signal-reference beam pair configuration. A spatial separation or alignment offset between the fibers causes the collimated beams 422, 424 to travel at an angle to each other at location 460. The tilt angle θ operates to produce a time delay between the beams 422, 424 that depends on transverse location. The beams 422, 424 produce an interference fringe or localized fringe pattern 480 transverse to the propagation direction that has high amplitude only in a region near where the beam delays are sufficiently equal. Accordingly, a single signal-reference beam pair in an AMOCT system can produce a transverse fringe pattern at a single frequency. As discussed elsewhere herein, the angle θ between the two beams can confer or contribute to a particular beat note or spatial period in the interference.

AMOCT system 400 also includes a detection mechanism 490, such as a linear array detector. The detector can be provided with sufficiently small detector spacing, so as to sample the interfering beams along the fringe direction to capture the fringe pattern 480, and thus the "echo" signal associated with the signal-reference beam pair. The transverse location of the maximum amplitude in the fringe pattern 480 can contain the depth information for the echo being detected. The fringe pattern spatial frequency can be determined based on the center wavelength of the SLD, the distance between the fibers, and the focal length of the lens.

In cases where the reference beam 424 is much stronger than the signal beam 422, the fringe pattern 480 may reside upon a large DC background caused primarily by the reference beam 424. In such cases, the small fringe amplitude can be resolved and also demodulated by using a matched filter. This can be accomplished in the Fourier domain and result in a demodulated signal that peaks at the time delay corresponding to the depth where the signal beam was reflected or scattered.

According to some embodiments, it is possible to combine multiple signal beams with a single reference beam. Where individual signal beams have respective unique carrier frequencies, and where different angles are used for individual signal beam, it is possible to simultaneously measure fringes from multiple signal-reference pairs by using matched filters tuned to each carrier frequency. Such matched filters may be designed to preferentially transmit interference signals at spatial frequencies about a single pair of beams while suppressing those from other beam pairs. Because the linear detector can capture both the fringe amplitude and its phase, it is also possible to obtain enhanced depth resolution when the AMOCT signal has sufficient fidelity. According to some embodiments, AMOCT systems can use the phase information and provide depth resolution that is not limited to roughly equal the coherence length of the light source.

According to some embodiments, the angle of the signal beam(s) relative to the reference beam can be adjusted to approach, but not exceed, the Nyquist frequency of the linear detector while being sufficiently distinct in spatial frequencies such that the matched filters will allow their detection with little crosstalk. In some cases, at this limit, 4 pixels in the detector would correspond to a full wave of relative delay between the reference and signal beams. For example, a system operated at an SLD wavelength of 1 micron and a 8000 element detector would have a range span of 8000/4=2000 microns. Because an AMOCT system can simultaneously sample multiple signal beams, the effective range of an AMOCT system can exceed that of some other tomography systems (e.g. spectral domain OCT) with as few as 3 multiplexed signal beams. According to some embodiments, desirable scanning depths can be achieved by using wavelengths between about 1.3 μm and about 1.5 μm.

Multiple Signal-Reference Beam Pairs

FIG. 5 illustrates aspects of angular multiplexed optical coherence tomography (AMOCT) systems and methods according to embodiments of the present invention. As depicted here, the AMOCT system 500 includes a light source 510. The light source may be provided as a single source light mechanism, such as a super luminescent diode (SLD), which may be fiber-coupled. In some cases, light from the light source can be coupled into a fiber and split into two beams by a fiber coupler. As shown here, a fiber splitter 520 can be used to direct a signal or sample beam along a sample leg 530 toward a test object 532 (such as an eye) and a reference beam along a reference leg 540 toward a detector 542 such as an array detector. Here, the reference beam is delayed by running the reference beam through a delay mechanism 550. For example, the reference beam can be delayed a fixed amount by running the beam through additional fiber length and/or free space. The signal beam 522 is scattered or reflected from the test object 532 and re-injected into its fiber 523. The scattered or retro-reflected beam from the test object is then passed through a fiber circulator 537, and into a fiber splitter 539 which operates to divide the signal beam into multiple signal beams 522a, 522b, and 522c. As shown here, the reference beam 524 is not retro-reflected through its fiber nor is it recombined collinearly with a signal beam in the splitter. Rather, the reference beam is combined non-collinearly with multiple retro-reflected signal beams in free space at location 560. The signal beams 522a, 522b, and 522c and the reference beam 524 from their respective fibers are combined on a lens 570. In this sense, where multiple signal beams and one reference beam are used, the configuration can be considered to provide a multiple signal-reference beam pair configuration. A spatial separation or alignment offset between the fibers causes the collimated beams to travel at an angle to each other at location 560. The beams produce an overlap 580 of localized fringe patterns transverse to the propagation direction that has high amplitude only in a region near where the beam delays are sufficiently equal. Accordingly, a multiple signal-reference beam pair configuration in an AMOCT system can produce a complex transverse fringe pattern containing multiple frequencies.

As shown here, the sample leg signal beam can be separated by fiber splitter 539 and individual resulting beams processed with different delays (e.g τ1, τ2, and τ3). Hence, different net sample delays can be associated with respective location or angular differences relative to the reference leg beam 524. As discussed elsewhere herein, an angle between two light beams can contribute to a beat note or interference pattern or period. Here, where individual signal beams 522a, 522b, and 522c can have their own respective angle with the reference beam 524, it is possible to produce multiple beat notes or interference patterns or periods at the detector. For example, each signal-reference beam pair may have a corresponding angle, and thus a corresponding beat note. Put another way, where there are multiple signal beam fibers (e.g. emanating from splitter 539), and such fibers are at varying angles relative to the reference beam, then each signal-reference beam pair can produce a localized fringe pattern having its own associated beat note. Accordingly, one or more beat notes can be controlled by adjusting the corresponding angles of the signal-reference beam pairs. When considering the combined localized fringe patterns on the array detector (e.g. which may be overlapping with one another), it is possible to separate out, extract, or otherwise isolate individual fringe patterns therefrom using Fourier or filter techniques. In this way, it is possible to tune into a particular localized fringe pattern or channel, where each fringe pattern or channel is associated with a respective signal-reference beam pair angle, and where a spatial frequency of a respective fringe pattern or channel is a function of the respective angle. Relatedly, using these techniques it is possible to separate out or isolate interference patterns from one another. Accordingly, embodiments of the present invention encompass systems and methods for tuning into a certain beat note or associated fringe pattern or spatial period, and evaluating patient tissue at a depth corresponding to that beat note or fringe pattern or spatial period. For example, as shown in FIG. 5, the signal-reference beam pair of 522b-524 corresponds to a tissue depth at or near a posterior portion of the crystalline lens, and thus by analyzing the spatial frequency and/or fringe pattern associated with the 522b-524 beam pair, it is possible to evaluate tissue characteristics of the posterior lens. As shown here, it is possible to simultaneously detect multiple localized fringe patterns at the array detector. Hence, it is possible to simultaneously analyze patient tissue or related structures or interfaces at multiple depths simultaneously, and/or throughout a broad tissue depth range.

As depicted in FIG. 5, it is possible to use different channels to probe at various depths within the eye, or across a wide depth range within the eye. In some cases, a signal-reference beam pair may operate to provide information throughout a depth range of about 5 mm to 10 mm. The entire depth of the eye may be about 30 mm. Hence, by using such a multiplexed approach, which involves the simultaneous detection of multiple localized fringe patterns, each associated with a delay and angle, it is possible to evaluate much or all of the eye tissue simultaneously. For example, evaluation of the anterior cornea can be associated with τ1 and/or the 522a-524 sample-reference angle, evaluation of the posterior lens can be associated with τ2 and/or the 522b-524 sample-reference angle, and evaluation of the retina can be associated with τ3 and/or the 522c-524 sample-reference angle. In this way, it is possible to provide a system having multiple OCT subsystems on a single device, and various channels can be used to evaluate various associated tissue depths.

Dual Collection Fiber With Static Focus System

Figure 6:
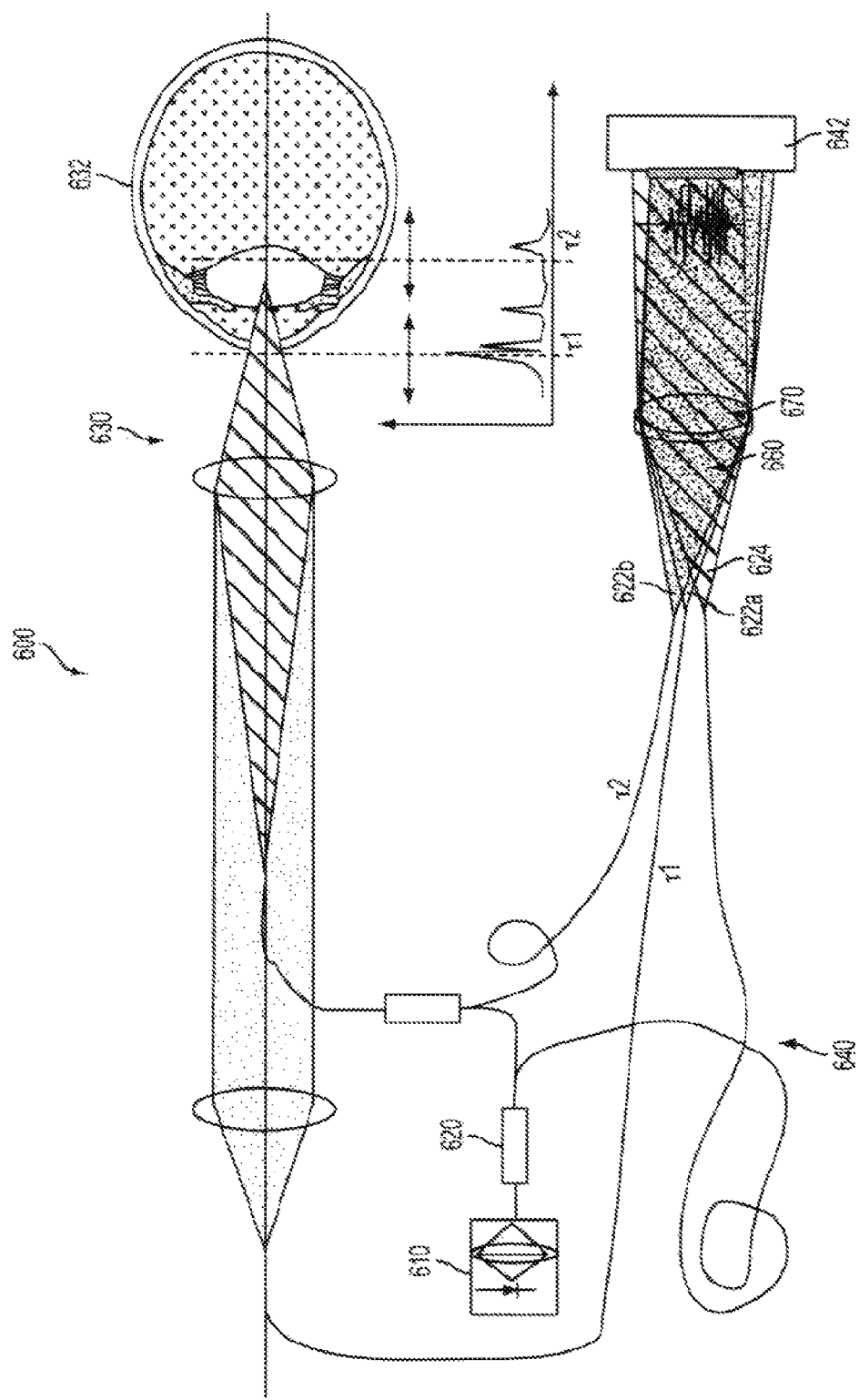

FIG. 6 illustrates aspects of angular multiplexed optical coherence tomography (AMOCT) systems and methods according to embodiments of the present invention. As depicted here, the AMOCT system 600 includes a light source 610. The light source may be provided as a single source light mechanism, such as a super luminescent diode (SLD), which may be fiber-coupled. In some cases, light from the light source can be coupled into a fiber and split into two beams by a fiber coupler. As shown here, a fiber splitter 620 can be used to direct a signal or sample beam along a sample leg 630 toward a test object 632 (such as an eye) and a reference beam along a reference leg 640 toward a detector 642 such as an array detector. According to some embodiments, scattered light corresponding to various sections of the eye can be collected on two fibers (Fiber L and Fiber $\tau 1$) with high efficiency using a static focus system. For example, Fiber L can serve to launch a probe beam such that it focuses in the lenticular region and collects light scattered therefrom. Further, Fiber $\tau 1$ and Lens 2 can be positioned to efficiently collect light scattered from the cornea and anterior chamber region because very little light is blocked by Fiber L. Such imaging conditions can provide high spatial resolution. One portion of the signal beam retro-reflected from the test object 632 is re-injected into Fiber L. Another portion of the signal beam retro-reflected from the test object 632 is re-injected into Fiber $\tau 1$. Accordingly, the signal beam can be divided into multiple signal beams 622a, 622b. As shown here, the reference beam 624 is not retro-reflected through its fiber nor is it recombined collinearly with a signal beam in the splitter. Rather, the reference beam is combined non-collinearly with multiple retro-reflected signal beams in free space at location 660. The signal beams 622a, 622b and the reference beam 624 from their respective fibers are combined on a lens 670.

As depicted here, the $\tau 1$ fiber light is processed through both lens 1 and lens 2. The $\tau 2$ fiber light is processed through lens 1 but not lens 2. Often, on the sample side, light returning back toward the detector can be scattered by the surfaces or tissues which are being interrogated. Hence, such scattered light may provide a weakened light signal. As shown here, light which is directed toward the object tissue is focused by lens 1, toward the interrogated location. Using lens 1 and lens 2, the returning light can then be collimated and efficiently collected into optical fiber for transmission toward the detector. As shown in the example here, light can be focused at two depths within the patient tissue, and respective returning light can be collected by two different fibers. For example, evaluation of the anterior cornea can be associated with $\tau 1$ and/or the 622a-624 sample-reference angle, and evaluation of the posterior lens can be associated with $\tau 2$ and/or the 622b-624 sample-reference angle. In this way, it is possible to efficiently collect and process light associated with multiple depths within the patient tissue, thus providing an extend depth range. Although FIG. 6 depicts the use of two different fibers for two different tissue depths, it is understood that multiple different fibers (e.g. more than two) can be used for evaluating multiple tissue depths (e.g. more than two). For example, a third fiber could be used to evaluate retinal tissue of the eye. In this way, it is possible to efficiently collect and process light associated with an extended depth range throughout the eye (or tissue or anatomy) without the use of a scanning system that involves scanning a focus to different depths throughout the tissue or anatomy. That is, light can be efficiently collected and processed for each individual channel, where a particular channel is associated with a particular depth or depth range.

Multi-Point

Figure 7:
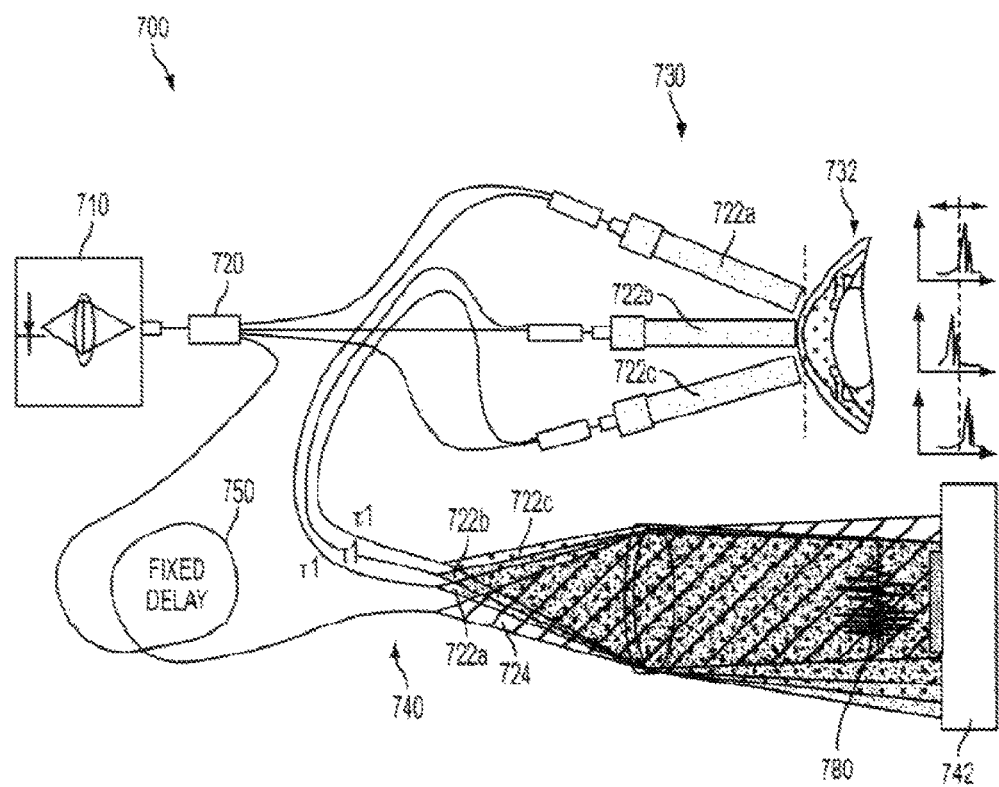

FIG. 7 illustrates aspects of angular multiplexed optical coherence tomography (AMOCT) systems and methods according to embodiments of the present invention. As depicted here, the AMOCT system 700 includes a light source 710. The light source may be provided as a single source light mechanism, such as a super luminescent diode (SLD), which may be fiber-coupled. In some cases, light from the light source can be coupled into a fiber and split into two beams by a fiber coupler. As shown here, a fiber splitter 720 can be used to direct one or more signal or sample beams along a sample leg 730 toward a test object 732 (such as an eye) and a reference beam along a reference leg 740 toward a detector 742 such as an array detector. Here, the reference beam is delayed by running the reference beam through a delay mechanism 750. For example, the reference beam can be delayed a fixed amount by running the beam through additional fiber length and/or free space. Individual signal beams 722a, 722b, 722c can be scattered or retro-reflected from the test object 732 and re-injected into or otherwise directed into respective fibers. As shown here, the reference beam 724 is not retro-reflected through its fiber nor is it recombined collinearly with a signal beam in the splitter. Rather, the reference beam is combined non-collinearly with multiple retro-reflected signal beams 722a, 722b, 722c in free space at location 560. The signal beams 722a, 722b, and 722c and the reference beam 724 from their respective fibers are combined on a lens 770. The beams produce an overlap 780 of localized fringe patterns transverse to the propagation direction that has high amplitude only in a region near where the beam delays are sufficiently equal. Hence, multiple signal-reference beam pairs can probe different transverse locations simultaneously. According to some embodiments, an AMOCT system can involve signal beams generated from different return beams, as in different locations on the cornea, but with small or no delays between them. Such configurations can be used for multipoint corneal topography and simultaneous pachymetry. According to some embodiments, signal beam origins from various embodiments can be combined to enable biometric and multipoint CT and pachymetry.

According to some embodiments, a detection mechanism such as a linear array detector may have multiple (e.g. up to four or more) linear arrays in each package. Such arrays may be similar to those used in color scanner applications. The use of additional individual linear arrays can operate to provide additional channels of detection.

In the embodiment depicted in FIG. 7, the sample leg involves multiple signal beams 722a, 722b, 722c at respective angles to object or patient anatomy. Each of the associated signal beams have a common delay (e.g. $\tau 1$). Hence, it is possible to evaluate tissue at a certain distance (e.g. across a common depth range for each channel), albeit at different locations on the patient tissue. For example, it is possible to probe or evaluate the cornea, at a given common depth, at different locations (e.g. three locations) across the cornea. In some cases, it is possible to measure relative positions of different parts of the cornea. According to the embodiment shown here, it is possible to obtain corneal topography information, such as shape information for the corneal surface. In some cases, it is possible to measure or evaluate a common tissue or structure at different locations thereof. For example, using this technique it is possible to evaluate the iris at three different locations. Accordingly, this technique can be used for measuring or evaluating the tilt of the eye, including real-time measurements. In some cases, this technique can be used to implement an eye tracking device or method (e.g. six axis eye tracker), whereby the eye position and/or tilt can be evaluated, and used to determine laser ablation pulse delivery protocols.

Sphero-Cylindrical Optical System and Linear Detector

FIG. 8 depicts aspects of angular multiplexed optical coherence tomography (AMOCT) systems and methods according to embodiments of the present invention. As shown here, a sphero-cylindrical optical system can provide a good match with a linear detector.

In use, the lens configuration shown here can operate to focus light so that it impinged upon the array detector (e.g. linear CCD) in a concentrated manner. The detector shown here is a line detector configuration, with a short height (side view) and a long width (top view). Use of the cylindrical lens allows a large amount of light to be concentrated on the detector, thus providing a highly efficient optical system. As shown in the side view, light emanating from the test object fiber and reference leg fiber combines to fill the spherical achromat lens, and is then focused tightly by the cylindrical achromat lens onto the thin linear CCD detector. As seen in the top view, the object and reference fibers are angularly displaced from one another, and th elight is combined to fill the spherical achromat lens. However, the cylindrical achromat does not operate to diminish the width of the combined beam in the same way that it operates to diminish the height of the combined beam. Accordingly, use of the cylindrical achromat allows the system to direct a large percentage of the combined light beams at the linear CCD.

Simulations

The Laboratory Virtual Instrumentation Engineering Workbench (LabVIEW) a system design platform and development environment was used to simulate aspects of AMOCT. In some instances, an interference pattern was calculated for multiple beams. In some instances, individual beams were assigned a respective power, angle, and relative delay. In some instances, matched filters were created for individual signal-reference pairs. In some instances, a combined detector signal was Fourier analyzed to extract the signals on each "channel".

Figure 9:
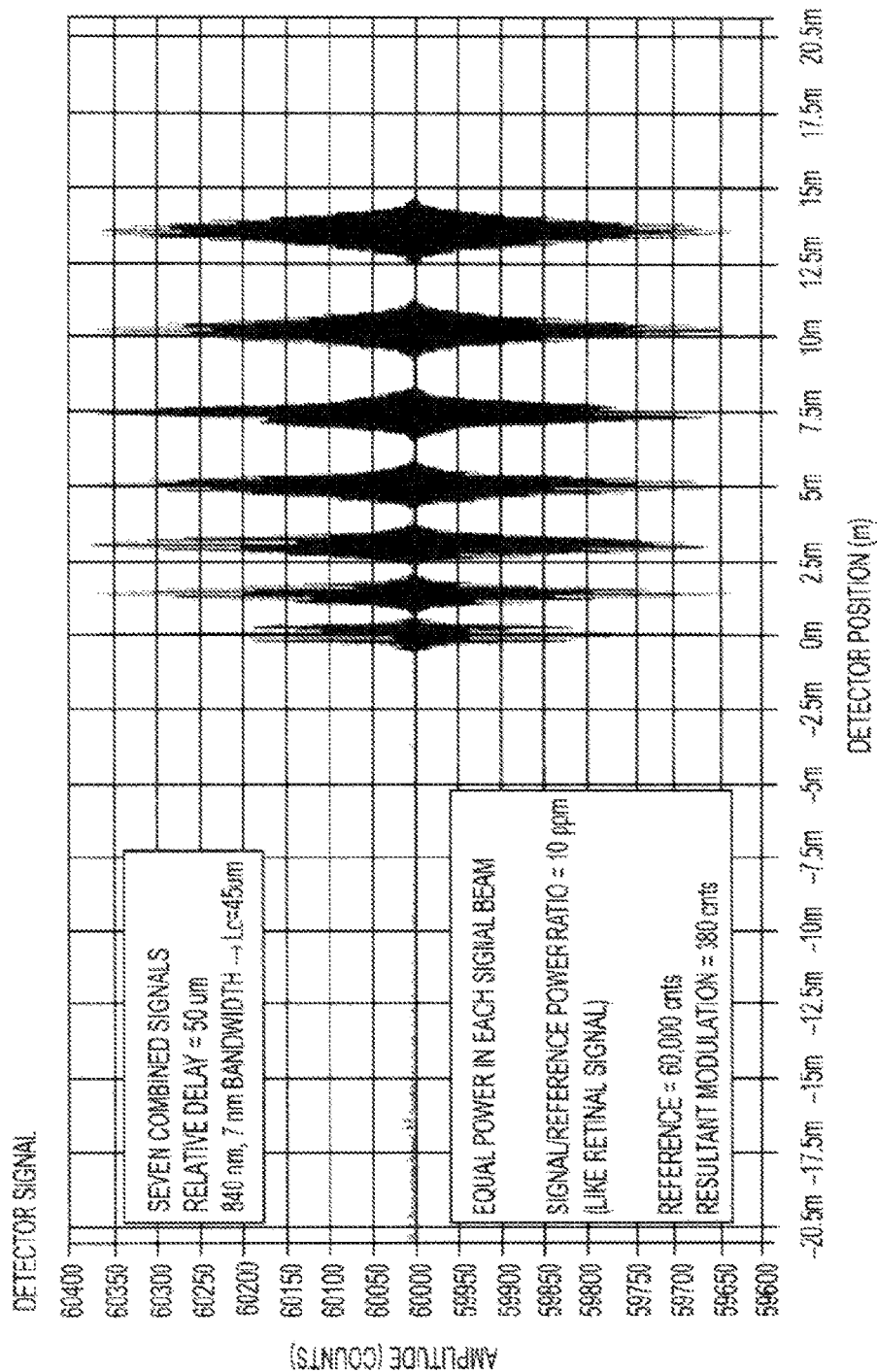

FIG. 9 depicts an exemplary detector signal simulation with seven angularly combined signals at 50 μm delay increments.

Figure 10:
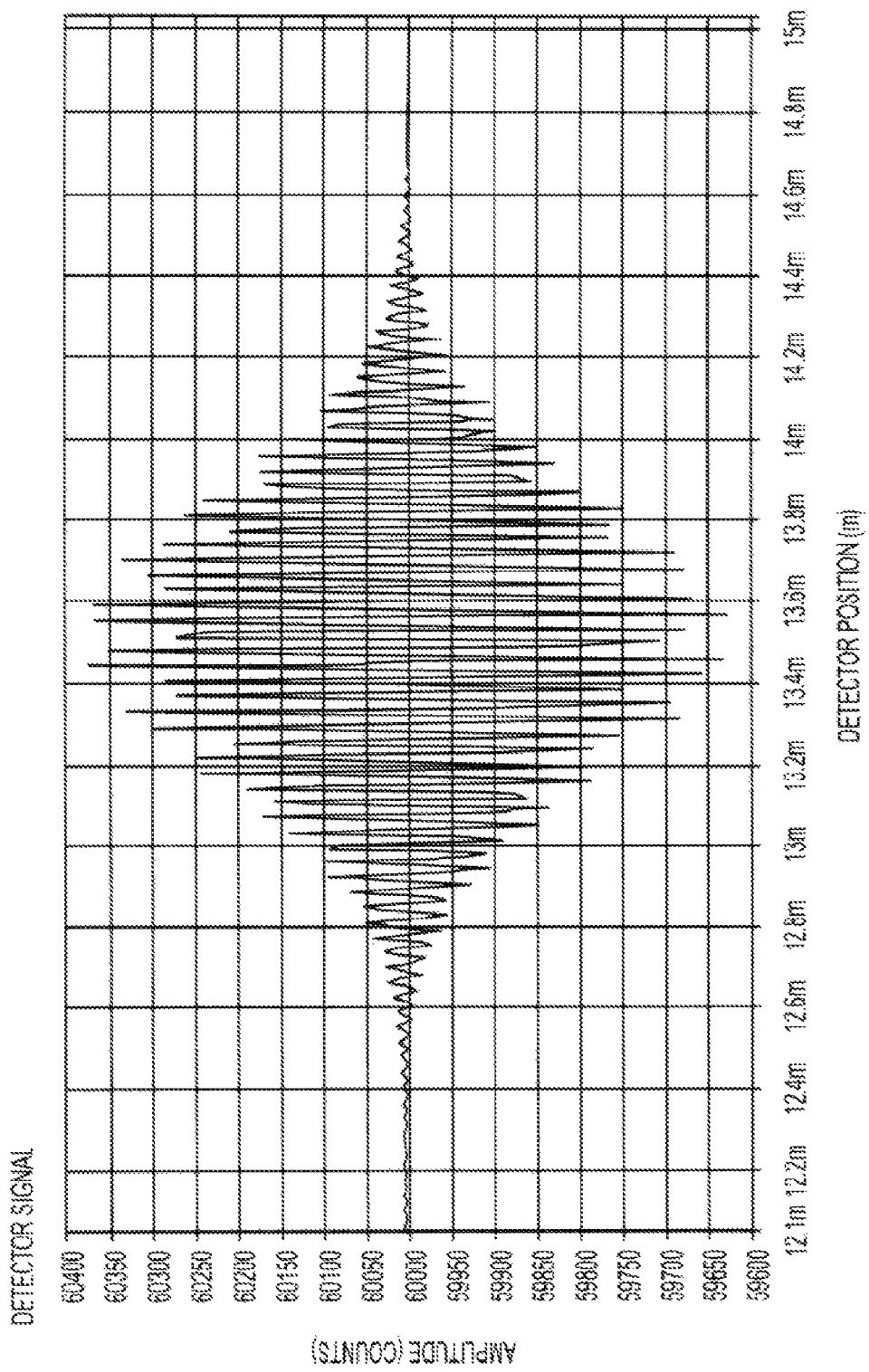
Figure 11:
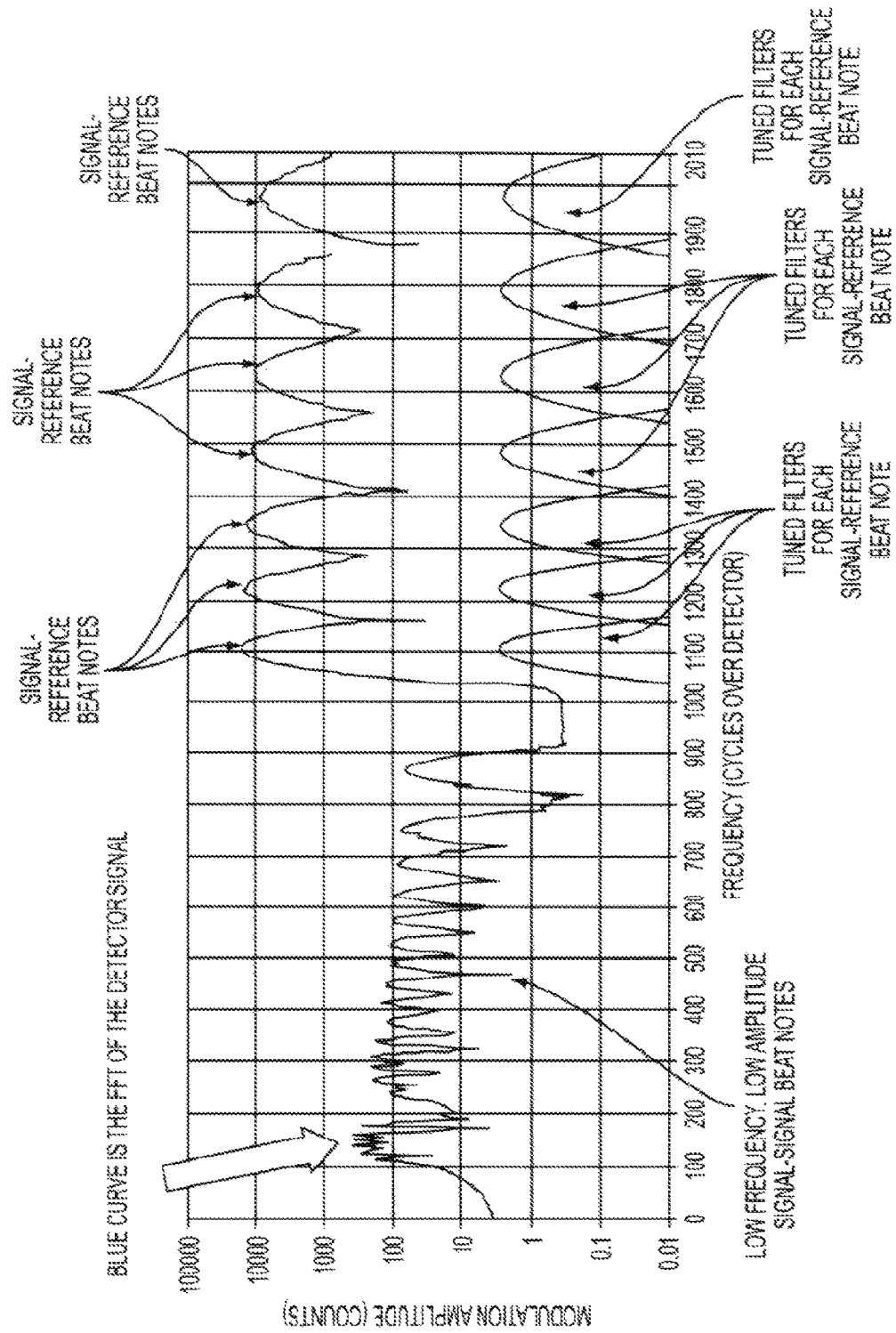

In the simulation depicted in FIG. 10, individual signals have a carrier frequency defined by their respective angle with the reference beam. Here the beam angle is 22.2 mR As illustrated in the simulation of FIG. 11, Fourier analysis of the signal can use filters tuned to individual carrier frequencies to resolve the individual signals. As shown here, various spatial frequencies can be evaluated. According to some embodiments, a spatial period or beat note can refer to an interference period or a period of an interference pattern. For example, when considering an interference pattern with alternating bright and dark sections, the spatial period can refer to the separation between adjacent bright sections (or between adjacent dark sections). In some cases, a spatial period can be considered as a difference or modulation between two combined closely related frequencies. For example, the spatial period can correspond to a modulation of intensity as measured by a detector.

Figure 12:
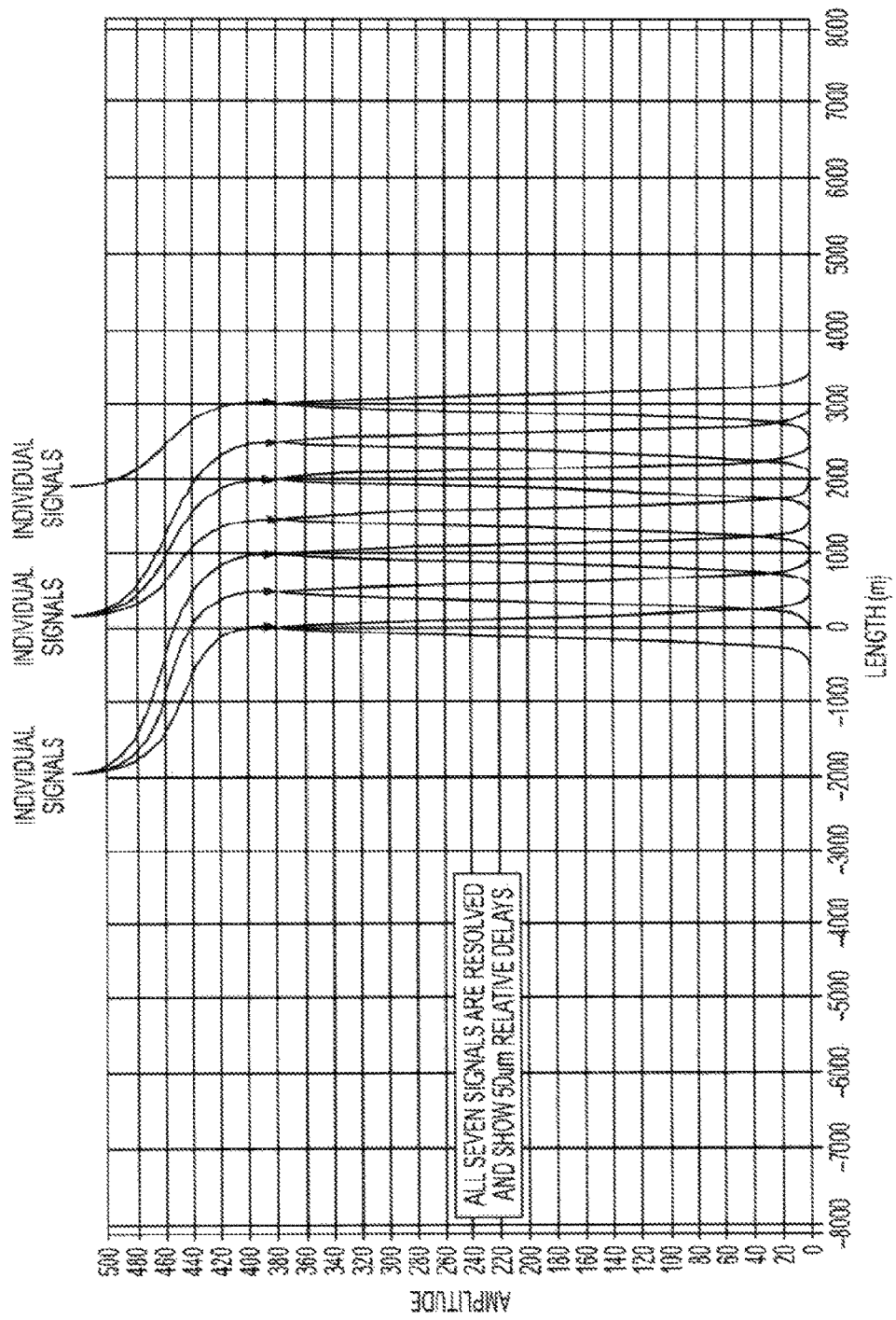

In the simulation embodiment of FIG. 12, it can be seen that individual AMOCT signals are resolved with high fidelity.

Figure 13:
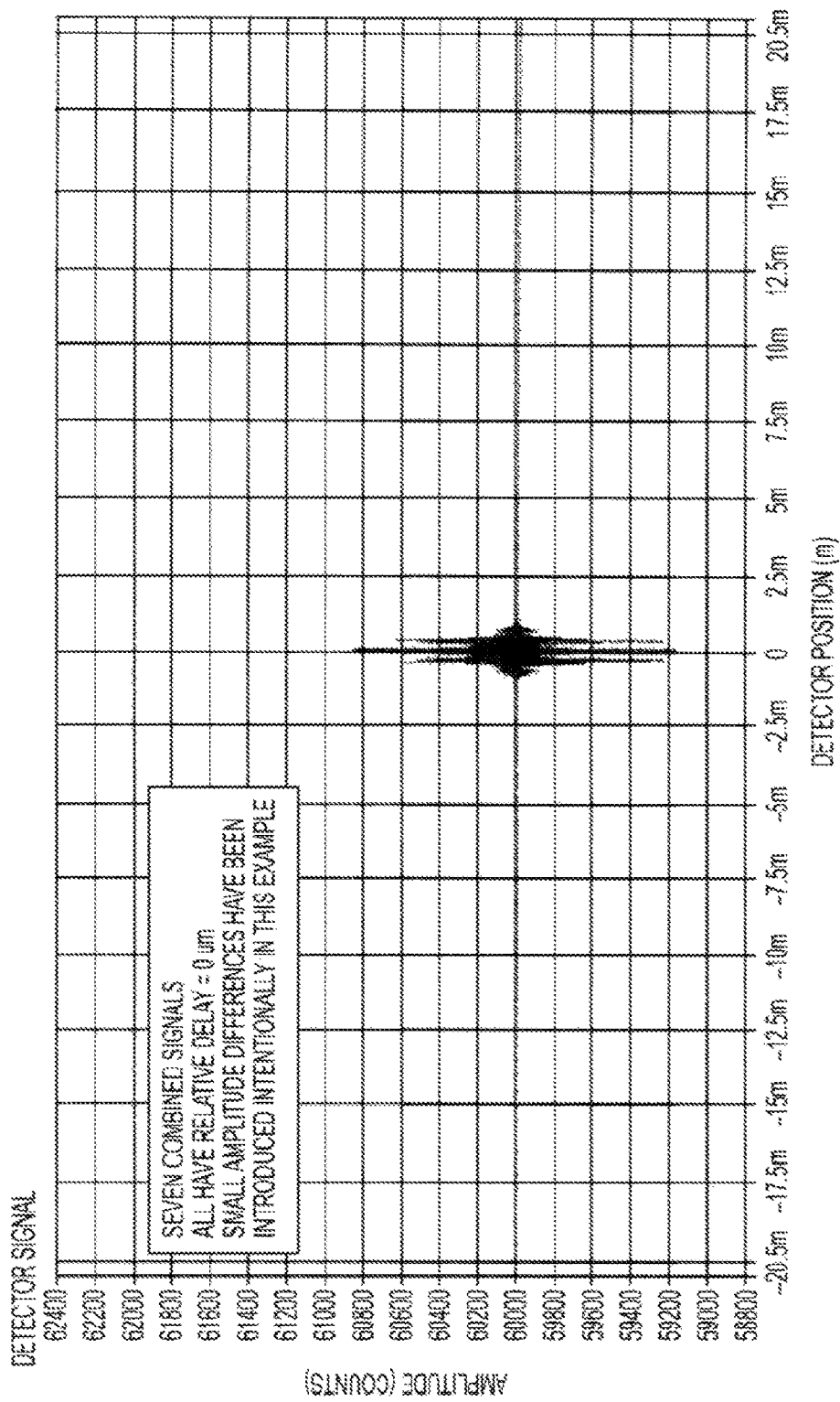

FIG. 13 shows an exemplary simulation, where individual signals (e.g. seven) may overlap completely on the detector, thus leading to a complex fringe pattern.

Figure 14:
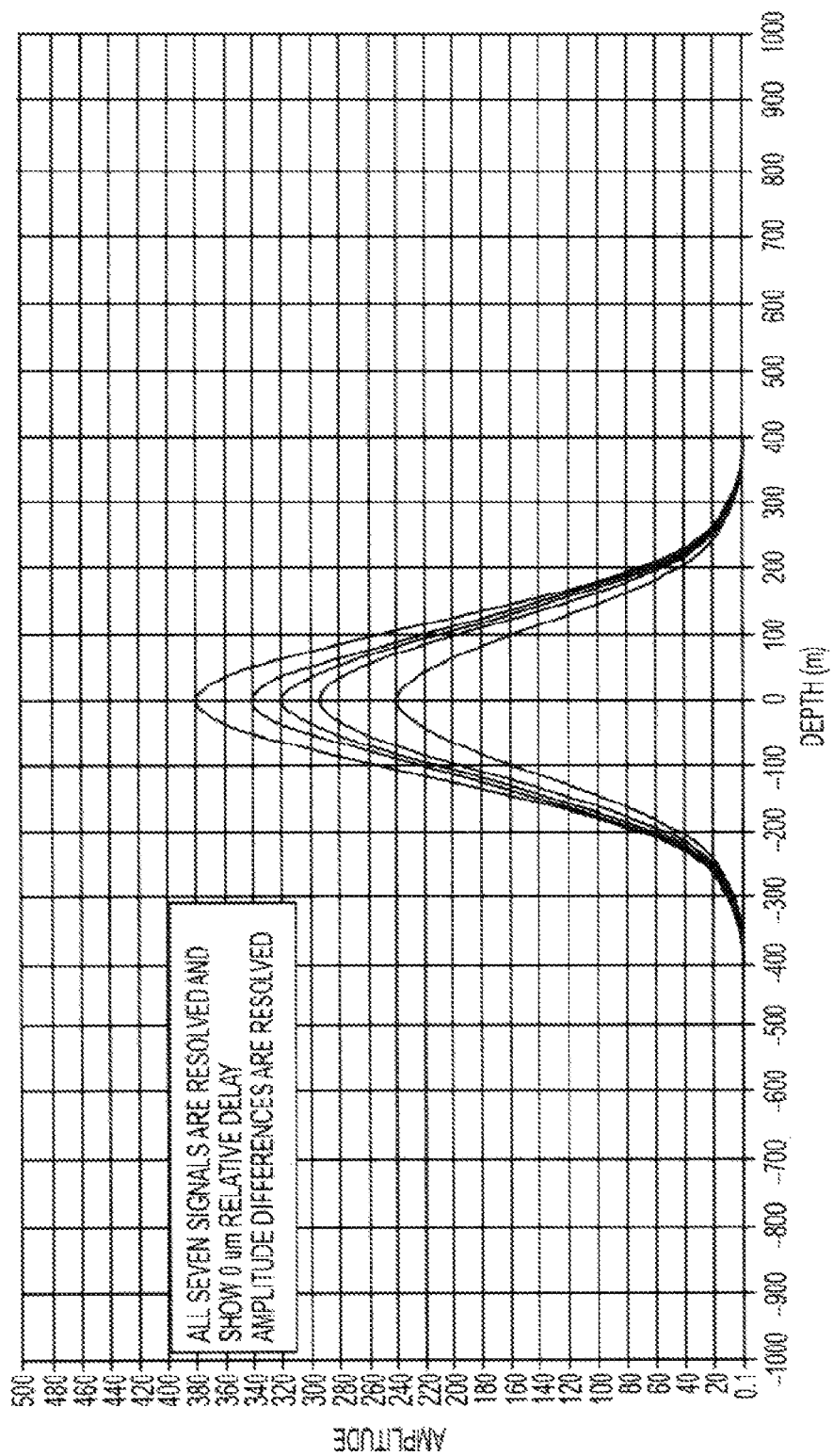

As shown in the FIG. 14 simulation, Fourier analysis of the complex fringe pattern can allow the individual signals to be resolved.

As illustrated by these simulations and as discussed elsewhere herein, AMOCT techniques can provide simultaneous detection of multiple signals on a single detector, and lower implementation costs as compared with other OCT technologies. Further, AMOCT embodiments can be implemented without using gratings, moving parts, PZT elements, sophisticated tunable light sources, or other features which may be associated with existing OCT technologies. What is more, AMOCT implementations can involve multiple signals configured to sample a large depth range or multiple selected smaller ranges. Still further, with certain AMOCT embodiments, there is no sign ambiguity in the tomography signal regarding the sign of the delay (e.g. positive and negative delays are handled). As discussed elsewhere herein, it is possible to use AMOCT to obtain a large effective depth range useful in simultaneous anterior chamber depth (ACD), lens thickness, axial length, or other optical feature measurements.

AMOCT systems and methods can be used in a variety of applications. For example, AMOCT can be incorporated with the use of femtosecond laser systems and methods for ocular surgery. Further, it is possible to use AMOCT techniques to locate the anterior corneal surface and reference it directly. Relatedly, it is possible to use AMOCT techniques to replace costly disposable standoff optics with lower cost, higher tolerance optics. Still further, it is possible to use AMOCT techniques to detect the crystal lens anterior or posterior surfaces for lens surgery. What is more, retinal surgeries associated with retinal re-attachment could be monitored in real time at multiple points during the surgery using AMOCT systems and methods.

Arrayed Angle-Multiplexed Optical Coherence Tomography (AAMOCT)

As discussed elsewhere herein angle-multiplexed OCT (AMOCT) can be used to acquire depth data from multiple regions simultaneously in a single cycle with a single beam, using light of a wavelength amenable to silicon detectors. In some cases, AMOCT techniques may involve scanning procedures to obtain two dimensional b-scans or three dimensional volumes.

Arrayed angle multiplexed OCT (AAMOCT) systems and methods can involve the integration of multiple interrogation beams into an AMOCT scheme. For example, a one dimensional array can be used to acquire a b-scan in one acquisition cycle, and a two dimensional array can be used to obtain a volumetric image in one cycle. This increased measurement throughput can allow for near real-time observations to be made. In some instances, the increased measurement throughput can enable the extraction of and use of aberrometry data. Due to the simultaneity of data acquisition across large volumes of the eye, AAMOCT is particularly suitable for applications in corneal topography, pachymetry, cataract characterization and LCS planning, intraocular lens treatment planning, eye tracking, range finding, iris registration, and the like.

Figure 15:
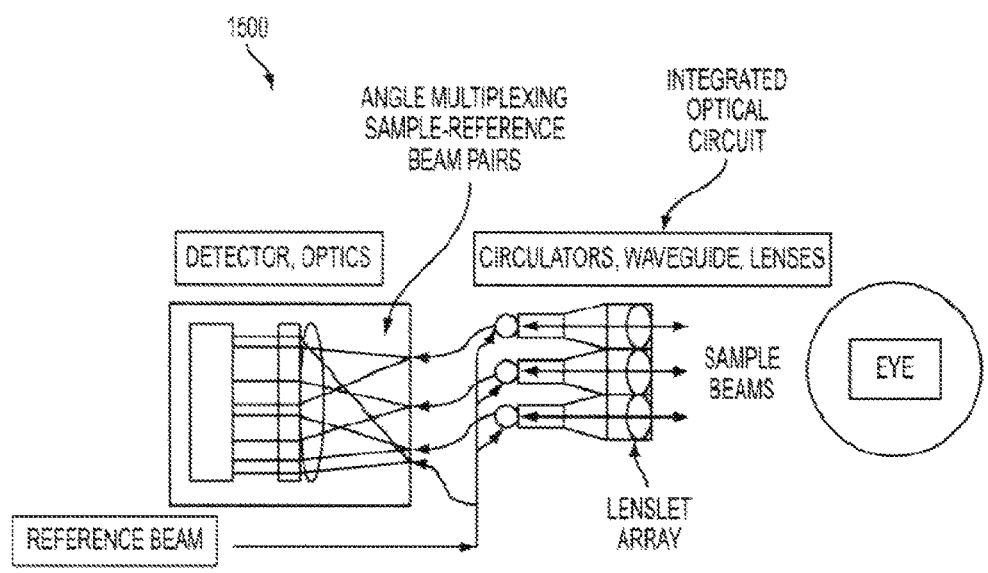

As depicted in FIG. 15, an exemplary AAMOCT system 1500 may include an integrated optical circuit (IOC) that includes micro-arrayed objective lenses, a waveguide, and optical circulators. Such An IOC device can be connected via a fiber bundle to an angle multiplexor, conditioning optics, and a CCD line detector. In some aspects, the system depicted in FIG. 15 can operate in an analogous way to the system depicted in FIG. 7.

According to some embodiments, an AAMOCT system may include a one dimensional integrated optical circuit, optionally in combination with additional scanning optomechanics to obtain volumetric data. In some embodiments, an AAMOCT system may include a two dimensional integrated optical circuit. According to some embodiments, an AAMOCT system may include the use of scanning optomechanics, for example if a single-spot sample density does not provide a sufficiently high spatial resolution for volumetric reconstruction. According to some embodiments, AAMOCT systems and methods may involve the incorporation of phase delays at one or more locations between reference and sample beams, for example in the integrated optical circuit, the fiber bundle, and/or the multiplexor.

According to some AAMOCT embodiments, the spatial resolution achieved by the system or method may be based on the based on the multitude of lenslets used. In some cases, each lenslet may operate to provide a separate channel, for the angle multiplexing. In this way, it is possible to interrogate multiple portions or spatial locations throughout the ocular structure, including the cornea, lens, retina, and the like. Each individual lenslet of the lenslet array can provide a respective beam. Exemplary lenslet arrays can include any desired number of lenslets, for example, 20, 100, or 1000 lenslets, where each lenslet provides a corresponding channel. In some cases, the system can operate to direct multiple sample beams toward the eye, such that different beams approach the eye at different angles (e.g. relative to an axis of the eye, such as the optical axis). In some cases, different beams can approach the eye at the same angle. The various sample beam angles impinging upon the eye can be based on the configuration of the lenslet array and/or the angle of the light which is directed into the lenslet array for transmission therethrough.

As shown in FIG. 15, the sample beams directed toward the eye are more or less parallel to one another, such that individual beams are directed to different portions of the eye. In some cases, one or more sample beams may be angularly offset from one another. In some cases, the system provides scattered light corresponding to various tissue locations, or various tissue or anatomical structure interfaces, and one or more of the sample beams may or may not not have a normal incidence relative to the corneal surface. According to some embodiments, there may be variation in the angle of incidence for individual sample beams propagated from the lenslet array toward the eye. In some cases, individual lenslets of the array may operate to focus light. In some cases, individual lenslets of the array may operate to collimate light. In some cases, one or more lenslets may have a common focal length. In some cases, individual lenslets may have different focal lengths. Various related combinations and permutations of lenslet array configurations (including individual lenslet size, spacing, optical power, position, and the like) are encompassed by embodiments of the present invention. In some cases, one or move individual lenslets may operate to weakly focus light across a broad depth of tissue or anatomy. In some cases, two or more individual lenslets may operate to focus light toward a common interrogation position, area, or depth range. In some cases, individual lenslets may operate to interrogate respective depth positions or ranges.

According to some embodiments, one or move individual lenslets can have diameters at micron level dimensions. For example, an individual lenslet may have a diameter of about 100 microns. Larger and smaller lenslet sizes are also contemplated. According to some embodiments, a fiber optic array can be used to direct light toward the lenslet array. Often, such an array of fibers is offset from the lenslet array at a certain distance. For example, the fiber array can be disposed one focal length away from the lenslet array. In some cases, by varying the distance or orientation between the fiber array and the lenslet array, it is possible to change the focus provided by the system. As shown here, multiple sample-reference beam pairs are angularly multiplexed at the detector mechanism. The embodiment depicted in FIG. 15 is well suited for use in obtaining spatially resolved measurements across the eye at multiple positions and/or depths simultaneously, without the use of a scanning mechanism (e.g. system involving galvanometrically controlled mirrors to provide dynamic angle adjustments). In some embodiments, the lenslet array may be a two dimensional array, for example a 10×10 lenslet array, a 100×100 lenslet array, or the like. In some cases, a lenslet array may provide individual lenslets that can be used to deliver interrogation beams across the entire diameter or area of the eye. In this way, it is possible to interrogate multiple points or positions at one time, and to obtain a full snapshot of the eye at all locations therethrough. Often, such systems may provide spatial resolution measurements involving an accuracy or precision on the order of 20 microns.

AMOCT and AAMOCT techniques as disclosed herein are well suited for use in ophthalmological applications, as well as optical metrology, and subcutaneous and vascular inspection applications, as well as subsurface interrogation of any of a variety of materials, substances, or structures.

The methods and apparatuses of the present invention may be provided in one or more kits for such use. The kits may comprise a system for evaluating an optical feature of a patient eye, and instructions for use. Optionally, such kits may further include any of the other system components described in relation to the present invention and any other materials or items relevant to the present invention. The instructions for use can set forth any of the methods as described above.

Each of the calculations or operations described herein may be performed using a computer or other processor having hardware, software, and/or firmware. The various method steps may be performed by modules, and the modules may comprise any of a wide variety of digital and/or analog data processing hardware and/or software arranged to perform the method steps described herein. The modules optionally comprising data processing hardware adapted to perform one or more of these steps by having appropriate machine programming code associated therewith, the modules for two or more steps (or portions of two or more steps) being integrated into a single processor board or separated into different processor boards in any of a wide variety of integrated and/or distributed processing architectures. These methods and systems will often employ a tangible media embodying machine-readable code with instructions for performing the method steps described above. Suitable tangible media may comprise a memory (including a volatile memory and/or a non-volatile memory), a storage media (such as a magnetic recording on a floppy disk, a hard disk, a tape, or the like; on an optical memory such as a CD, a CD-R/W, a CD-ROM, a DVD, or the like; or any other digital or analog storage media), or the like.

All patents, patent publications, patent applications, journal articles, books, technical references, and the like discussed in the instant disclosure are incorporated herein by reference in their entirety for all purposes.

While the above provides a full and complete disclosure of the preferred embodiments of the present invention, various modifications, alternate constructions and equivalents may be employed as desired. Therefore, the above description and illustrations should not be construed as limiting the invention, which can be defined by the appended claims.

What is claimed is:

1. An angle multiplexed optical coherence tomography system for evaluating an eye of a patient, the system comprising:
    a light source;
    an optical assembly for obtaining a reference beam and obtaining a plurality of sample beams which have passed through the eye of the patient and which correspond to respective anatomical locations of the eye of the patient; and
    a detection mechanism having a receiving surface,
    wherein the optical assembly directs the plurality of sample beams and the reference beam to be incident on the receiving surface of the detector mechanism at respective incident angles that are different from one another, and wherein the detection mechanism detects individual unique interference patterns respectively provided by the plurality of sample beams, for simultaneous evaluation of the anatomical locations.

2. The system according to claim 1, wherein individual sample beams provide respective unique interference spatial periods at the detection mechanism.

3. The system according to claim 2, wherein unique interference spatial periods are adjustable in response to changes in respective sample beam incident angles relative to the reference beam.

4. The system according to claim 1, wherein the optical assembly includes one or more collimation lenses that direct combined sample-reference beam pairs toward the detection mechanism.

5. The system according to claim 1, wherein the system provide an accuracy for range finding on the order of 10 microns.

6. The system according to claim 1, further comprising a filter assembly that transmits interference signals at spatial frequencies about a first sample-reference beam pair and suppresses interference signals at spatial frequencies about a second sample-reference beam pair.

7. An optical coherence tomography system for evaluating an eye of a patient, the system comprising:
    a light source; and
    an optical assembly for obtaining a reference beam and obtaining a sample beam which has passed through the eye of the patient and which corresponds to an anatomical location of the eye of the patient, including a lens that receives the sample beam and the reference beam as a pair of beams combined at a non-zero angle relative to each other, and directs the combined sample-reference beam pair toward a detection mechanism that detects an interference pattern provided by the beam pair for evaluation of the anatomical location.

8. An angle multiplexed optical coherence tomography method for evaluating an eye of a patient, comprising:
    obtaining a reference beam;
    obtaining a plurality of sample beams which have passed through the eye of the patient and which correspond to respective anatomical locations of the eye of the patient;
    directing the plurality of sample beams and the reference beam to be incident on a receiving surface of a detector mechanism at respective incident angles that are different from one another;
    detecting, by the detector mechanism, individual unique interference patterns respectively provided by the plurality of sample beams; and
    evaluating the eye of the patient based on the detected interference patterns.

9. The method according to claim 8, further comprising positioning a corneal topography system relative to the eye based on the evaluation, and obtaining a corneal topography measurement of the eye.

10. The method according to claim 9, wherein the topography measurement is performed without aligning the corneal topography system using corneal topography fiducials.

* * * * *